United States Patent
Blank et al.

(10) Patent No.: US 9,714,249 B2
(45) Date of Patent: Jul. 25, 2017

(54) PYRAZOLO-PYRROLIDIN-4-ONE DERIVATIVES AND THEIR USE IN THE TREATMENT OF DISEASE

(71) Applicants: Jutta Blank, Binzen (DE); Simona Cotesta, Basel (CH); Vito Guagnano, Basel (CH); Heinrich Rueger, Flueh (CH)

(72) Inventors: Jutta Blank, Binzen (DE); Simona Cotesta, Basel (CH); Vito Guagnano, Basel (CH); Heinrich Rueger, Flueh (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/892,628

(22) PCT Filed: May 27, 2014

(86) PCT No.: PCT/IB2014/061743
§ 371 (c)(1),
(2) Date: Nov. 20, 2015

(87) PCT Pub. No.: WO2014/191911
PCT Pub. Date: Dec. 4, 2014

(65) Prior Publication Data
US 2016/0096843 A1    Apr. 7, 2016

(30) Foreign Application Priority Data

May 28, 2013    (EP) ..................... 13169448

(51) Int. Cl.
| | | |
|---|---|---|
| *C07D 487/04* | (2006.01) | |
| *A61K 31/4439* | (2006.01) | |
| *A61K 31/444* | (2006.01) | |
| *A61K 31/506* | (2006.01) | |

(52) U.S. Cl.
CPC .......... *C07D 487/04* (2013.01); *A61K 31/444* (2013.01); *A61K 31/4439* (2013.01); *A61K 31/506* (2013.01)

(58) Field of Classification Search
CPC .................................................... C07D 487/04
USPC ...................................... 546/275.7; 514/338
See application file for complete search history.

(56) References Cited

U.S. PATENT DOCUMENTS

| | | | |
|---|---|---|---|
| 3,829,420 A | 8/1974 | Inaba et al. | |
| 3,865,827 A | 2/1975 | Yamamoto et al. | |
| 3,923,710 A | 12/1975 | Ishizumi et al. | |
| 4,099,002 A | 7/1978 | Inaba et al. | |
| 4,258,187 A | 3/1981 | Middleton | |
| 4,335,127 A | 6/1982 | Vandenberk et al. | |
| 4,695,633 A | 9/1987 | Berneth et al. | |
| 6,479,499 B1 | 11/2002 | Kuo et al. | |
| 6,734,302 B2 | 5/2004 | Kong et al. | |
| 7,541,354 B2 | 6/2009 | Fancelli et al. | |
| 8,101,644 B2 | 1/2012 | Kai et al. | |
| 8,222,288 B2 | 7/2012 | Wang et al. | |
| 8,440,693 B2 | 5/2013 | Berghausen et al. | |
| 2003/0153580 A1 | 8/2003 | Kong et al. | |
| 2006/0069085 A1 | 3/2006 | Zhao et al. | |
| 2008/0153791 A1 | 6/2008 | Wilckens | |
| 2009/0163545 A1 | 6/2009 | Goldfarb | |
| 2010/0160356 A1 | 6/2010 | Heinrich et al. | |
| 2010/0210632 A1 | 8/2010 | Kai et al. | |
| 2011/0183939 A1 | 7/2011 | Kai et al. | |
| 2011/0230457 A1 | 9/2011 | Berghausen et al. | |
| 2011/0301133 A1 | 12/2011 | Wu et al. | |
| 2012/0065210 A1 | 3/2012 | Chu et al. | |
| 2013/0245036 A1 | 9/2013 | Berghausen et al. | |
| 2013/0281396 A1 | 10/2013 | McLure et al. | |
| 2013/0281473 A1 | 10/2013 | Berghausen et al. | |
| 2013/0317024 A1 | 11/2013 | Cotesta et al. | |
| 2014/0011798 A1 | 1/2014 | Furet et al. | |
| 2014/0135306 A1 | 5/2014 | Buschmann et al. | |

FOREIGN PATENT DOCUMENTS

| | | |
|---|---|---|
| EP | 1657238 A1 | 5/2006 |
| EP | 2 143 713 A1 | 1/2010 |
| JP | 45-16950 A | 6/1970 |

(Continued)

OTHER PUBLICATIONS

Acharya, B.P. et al., "Friedel-Crafts Acylation with 2-Isocyanatobenzoyl Chlorides: The Structure of the Intermediate Complex," Journal of Chemical Research, Synopses, (4):96-7 (1987)[Abstract only].
Bahloul, A. et al., "1,3-Dipolar Cycloaddition of Diarylnitrilimines with 4-Arylidene-1,2-Diphenyl-1,4-Dihydro-3(2H)-Isoquinolin-3-Ones," Journal de la Societe Marocaine de Chimie, 2(1):12-17 (French)(1993)[Abstract only].
Chen, R. et al., "Ytterbium(III) Triflate-Catalyzed Stereoselective Synthesis of Beta-lactams via [2+2] Cyclocondensation in Ionic Liquid," Synthetic Communications, 36(21):3167-3174, Taylor & Francis Group, LLC (English)(2006).
De Luca et al., "3D Pharmacophore Models for 1,2,3,4-Tetrahydroisoquinoline Derivatives Acting as Anticonvulsant Agents" Arch. Pharm. Chem. Life Sci., 2006, 339, 388-400.

(Continued)

*Primary Examiner* — Patricia L Morris
(74) *Attorney, Agent, or Firm* — Scott W. Reid

(57) ABSTRACT

The present invention provides a compound of formula (I) or a pharmaceutically acceptable salt thereof; a method for manufacturing the pyrazolo-pyrrolidin-4-one derivatives, and their use as BET inhibitors for the treatment of conditions or diseases such as cancer. The present invention further provides a combination of pharmacologically active agents and a pharmaceutical composition.

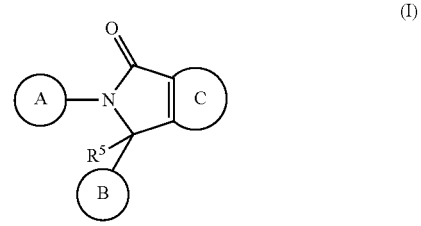

(I)

6 Claims, No Drawings

(56) References Cited

FOREIGN PATENT DOCUMENTS

| | | |
|---|---|---|
| JP | 46-15500 A | 4/1971 |
| JP | 57021388 | 2/1982 |
| JP | 2001302515 A | 10/2001 |
| JP | 2005-511766 A | 4/2005 |
| JP | 2006-524228 | 10/2006 |
| JP | 2014-533745 | 12/2014 |
| WO | 93/04047 A1 | 3/1993 |
| WO | 95/19362 A1 | 7/1995 |
| WO | 98/19362 A1 | 7/1995 |
| WO | 98/01467 A2 | 1/1998 |
| WO | 98/45276 A2 | 10/1998 |
| WO | 00/66560 A1 | 11/2000 |
| WO | 02/12242 A2 | 2/2002 |
| WO | 03/051359 | 6/2003 |
| WO | 03/062392 A2 | 7/2003 |
| WO | 03/095625 A2 | 11/2003 |
| WO | 03/101985 A1 | 12/2003 |
| WO | 2004/014916 | 2/2004 |
| WO | 2004/014916 A1 | 2/2004 |
| WO | 2004/094421 A1 | 11/2004 |
| WO | 2004/094429 A1 | 11/2004 |
| WO | 2004/096134 A2 | 11/2004 |
| WO | 2005/027882 A1 | 3/2005 |
| WO | 2005/051922 A1 | 6/2005 |
| WO | 2005/110996 A1 | 11/2005 |
| WO | 2005/117876 A1 | 12/2005 |
| WO | 2006/024837 A1 | 3/2006 |
| WO | 2006/074262 A1 | 7/2006 |
| WO | 2006/097337 A1 | 9/2006 |
| WO | 2006/100038 A1 | 9/2006 |
| WO | 2006/136606 A2 | 12/2006 |
| WO | 2007/068637 A1 | 6/2007 |
| WO | 2007/096334 A1 | 8/2007 |
| WO | 2007/144384 A1 | 12/2007 |
| WO | 2008/034039 A2 | 3/2008 |
| WO | 2008/045529 A1 | 4/2008 |
| WO | 2008/120725 A1 | 10/2008 |
| WO | 2008/130614 A2 | 10/2008 |
| WO | 2010/007116 A2 | 1/2010 |
| WO | 2010/035727 A1 | 4/2010 |
| WO | 2010/047956 A1 | 4/2010 |
| WO | 2010/141738 A2 | 12/2010 |
| WO | 2011/076786 A1 | 6/2011 |
| WO | 2011/161031 A1 | 12/2011 |
| WO | 2012/034954 A1 | 3/2012 |
| WO | 2012/046030 A2 | 4/2012 |
| WO | 2012/065022 A2 | 5/2012 |
| WO | 2012/151512 A2 | 11/2012 |
| WO | 2012/174487 A2 | 12/2012 |
| WO | 2012/175487 A2 | 12/2012 |
| WO | 2012/175520 A1 | 12/2012 |
| WO | 2013/027168 A2 | 2/2013 |
| WO | 2013/033268 A2 | 3/2013 |
| WO | 2013/033270 A2 | 3/2013 |
| WO | 2013/080141 A1 | 6/2013 |
| WO | 2013/097052 A1 | 7/2013 |
| WO | 2013/111105 A1 | 8/2013 |
| WO | 2013/156869 A1 | 10/2013 |
| WO | 2013/158952 A1 | 10/2013 |
| WO | 2013/175281 A1 | 11/2013 |
| WO | 2013/175417 A1 | 11/2013 |
| WO | 2014/191911 A1 | 12/2014 |

OTHER PUBLICATIONS

Dietz, G. et al.; "Synthesis and Conversion of 3,4-Dihydroquinazolin-4-ols. Part 2: Conversion of 3,4-Dihydroquinazolin-4-ols;" Direktionsber. Forsch. Entwickl., VEB Pharm. Komb. Germed Dresden, Dresden, Ger. Dem. Rep.; Pharmazie; 35(12):751-5 (German)(1980)[Abstract only].

Dudkina, Anna S. et al. "Small Molecule Protein-Protein Inhibitors for the p53-MDM2 Interaction", Current Topics in Medicinal Chemistry, 2007, 7, pp. 952-960.

Ishiwaka, N. et al., "o-Aminobenzophenone Derivatives. V. Reactions of 2-Amino-5-Chloro-Benzophenone with Isocyanates and Isothiocyanates," Kagaku Zasshi, 90(9):917-20 (Japanese)(1969)[Abstract only].

Ishiwaka, N. et al., "Reaction of 2-Amino-5-Chlorobenzophenone with P-Substituted Phenyl Isocyanates," Kagaku Zasshi, 91(10):994-7 (Japanese)(1970)[Abstract only].

Ivanov et al., Polyphosphoric acid-induced construction of quinazolinone skeleton from 1-(3,4-dimethoxyphenyl)-3-phenylurea and carboxylic acids. Heterocycles. May 12, 2006;68(7):1443-9.

Ivanov, I., "Synthesis of 6,7-Dimethoxy-3,4-Diphenyl-2(1H)-Quinazolinone from 1-(3,4-Dimethoxyphenyl)Urea and Benzoic Acid in Polyphosphoric Acid," Molbank M492/1-M492/2 (English)(2006)[Abstract only].

Mollov, N.M. et al., "Internal Alpha-Amidoalkylation Leading to 1,4-Dihydro-3(2H)-Isoquinolinones," Acta Chimica Academiae Scientiarum Hungaricae, 98(3):315-19 (English)(1978).

Mollov, N.M. et al., "Reactivity of Adducts Obtained from Arylacetyl Chloride and Aromatic Schiff Bases," Izvestiya po Khimiya, 10(4):616-20 (English)(1977).

Mollov, N.M. et al., "Synthesis of 3(2H)-isoquinolinones by Means of Inner Alpha-Amidoalkylation," Doklady Bolgarskoi Akademii Nauk, 28(8):1055-7 (English)(1975)[Abstract only].

Mumm, O. et al., "Diacylamides," Berichte der Deutschen Chemischen Gesellschaft, 48:379-91 (1915)[Abstract only].

Pfeiffer, P. et al., "Autoxidation Phenomena in the Anils of the Indandione Series. II," Journal fuer Praktische Chemie (Leipzig), 159:13-35 (1941)[Abstract and Article].

Pfeiffer, P. et al., "Autoxidation Phenomena. VI," Justus Liebigs Annalen der Chemie, 563:73-85 (1949)[Abstract and Article].

Pfeiffer, P. et al., "Autoxidation Reactions. VII," Justus Liebigs Annalen der Chemie, 581:149-59 (1953)[Abstract and Article].

Richter, D., "Anthraquinone Coloring Matters: Ruberythric Acid," Journal of the Chemical Society, 1701-3 (1936).

Richter, P. et al., "Synthesis of Derivatives of 2-Hydrazino-1,4- or 3,4-Dihydroquinazolines," Pharmazie, 45 (10):721-4 (German)(1990)[Abstract only].

Schonberg, A. et al., "Autoxidation Effects in the Indone Series," Naturwissenschaften, 24:620 (1936)[Abstract only].

Schonberg, A. et al., "Autoxidation Phenomena and Valency Tautomerism in the Indone Series," Journal of the Chemical Society, 109-12 (1937).

Shangary, Sanjeev et al., "Targeting the MDM2-p53 Interaction for Cancer Therapy", Clin. Cancer Res., 2008, 14, 5318-5324.

Venkov, A. et al., "An Improved Synthesis of N-Substituted 1-Aryl-3-Oxo-1,2,3,4-Tetrahydroisoquinolines," Synthesis, 216-17, Stuttgart, New York (English)(1982).

Ventsov, A. et al., "Synthesis of N-Substituted 1,4-Dihydro-3(2H)-Isoquinolinones from 3,4,5-Trimethoxyphenylacetyl chloride and Schiff Bases," Bolgarskoi Akademii Nauk, 34(10):1405-7 (English)(1981)[Abstract only].

Yamamoto, M. et al., "Synthetic Studies on Quinazoline Derivatives. II. The Reactions of 2-Trichloro- and 2-Trifluoroacetamidobenzophenones with Primary Amines," Chemical & Pharmaceutical Bulletin, 29(8):2135-56 (English)(1981).

Zhang, Y. et al., "Superacid-Promoted Reactions of N-Acyliminium Ions: An Effective Route to Substituted 3-Oxo-1,2,3,4-Tetrahydroisoquinolines and Related Products," Synthesis (11):1775-1780 (English)(2006).

Zin'Kovskaya, V.R. et al., "Ring-chain transformations involving the carbonyl group. XVI. Amides of 2-benzoylphenyl-Alpha,Alpha-dimethylacetic acid," Latvijas PSR Zinatnu, Akademijas Vestis, Kimijas Serija, (1)65-8 (Russian)(1976)[Abstract only].

Sheng, R. et al, Pharmacophore model construction of p53-MDM2 binding inhibitors, Acta Physico-Chimica Sinica, Aug. 6, 2007, vol. 23, No. 11,p. 1815-1820.

Aebi, A. et al, Pharmaceutica Acta Helvetiae, vol. 38, Issue: 7-8, pp. 616-22, Journal, 1963.

Shams El-Dine, S. A et al Pharmazie, vol. 56, Issue: 12, pp. 933-937, Journal, 2001.

(56) References Cited

OTHER PUBLICATIONS

Chaudhari, P.V., Oriental Journal of Chemistry (2012), 28(1), 507-512.
Journal of Enzyme Inhibition and Medicinal Chemistry (2011), 26(4), 472-479.
J. D. Akbari et al.: Indian Journal of Chemistry, Section B: Organic Chemistry Including Medicinal Chemistry (2008), 47B(3), 477-480.
Raj et al.: Organic Chemistry: An Indian Journal (2007), 3(4),176-179.
Ahmed Kamal et al.: Expert opinion on therapeutic patents 2012, vol. 22, No. 2, pp. 95-105, XP055107028.
Chung et al., Fragment-based discovery of bromodomain inhibitors part 1: inhibitor binding modes and implications for lead discovery. J Med Chem. Jan. 26, 2012;55(2):576-86.
Filippakopoulos et al., Benzodiazepines and benzotriazepines as protein interaction inhibitors targeting bromodomains of the BET family. Bioorg Med Chem. Mar. 15, 2012;20(6):1878-86.
Filippakopoulos et al., Selective inhibition of BET bromodomains. Nature. Dec. 23, 2010;468(7327):1067-73.
Hackam et al., Translation of research evidence from animals to humans. JAMA. Oct. 11, 2006;296(14):1731-2.
Jordan, Tamoxifen: a most unlikely pioneering medicine. Nat Rev Drug Discov. Mar. 2003;2(3):205-13.
Wu et al., The double bromodomain-containing chromatin adaptor Brd4 and transcriptional regulation. J Biol Chem. May 4, 2007;282(18):13141-5.
Andreichikov et al., Chemistry of Oxalyl Derivatives of Methyl Ketones XLIV. Synthesis of 4-Aroyl-1,5-Diphenyltetrahydropyrrole-2,3-Diones and their Reaction with Amines and Hydrazine. Journal of Organic Chemistry 1986;22(8):1572-7.
Dohrn et al., Berichte der Deutschen Chemischen Gesellschaft [Abteilung] B: Abhandlungen. 1931;64B:2863-5.
Gein et al., Reactions of 4-Acyl-1-alkoxyaryl-1-5-aryl-3-hydroxy-2,5-dihydro-1 H-pyrrol-2-ones with Nucleophilic Reagents. Russian Journal of Organic Chemistry. 2011;47(1):95-9.
Gein et al., 5-Membered 2,3-Dioxoheterocyclic Compounds. Journal of General Chemistry. 1993;63(10):2324-8.
Lee et al., Novel Pyrrolopyrimidine-Based alpha-Helix Mimetics: Cell Permeable Inhibitors of Protein-Protein Interactions. Journal of the American Chemical Society. 2010;133:676-9.
Miyazaki et al., Lead optimization of novel p53-MDM2 interaction inhibitors possessing dihydroimidazothiazole scaffold. Bioorganic and Medicinal Chemistry Letters. 2013;23:728-32.
No Auhtor Listed, WedMD "Leukemia." Available from: <http://www.webmd.com/cancer/tc/leukemia-prevention?print=true#> @2010.
No Author Listed, American Cancer Society. "Leukemia—Acute Myeloid (Myelogenous)." © 2013. Available from: <http://www.cancer.org/cancer/leukemia-acutemyeloidaml/detailedguide/leukemia-acute-myeloid-myelogenous-what-is-aml >.
No Author Listed, Mayo Clinic "Leukemia Medications." Available from: <http://www.drugs.com/condition/leukemia.html> @2013.
No Author Listed, National Cancer Institute. "Drugs Approved for Leukemia." © 2013. Available from: http://www.cancer.gov/cancertopics/druginfo/leukemia/print >.
Richter et al., An Optimised Small-Molecule Stabiliser of the 14-3-3-PMA2 Protein-Protein Interaction. Chem. Eur. J. 2012;18(21):6520-7.
Sun et al., Single-Nucleotide Polymorphisms in p53 Pathway and Aggressiveness of Prostate Cancer in a Caucasian Population. Clin. Cancer Res. 2010;16:5244-51.
Vanotti et al., Cdc7 Kinase Inhibitors: Pyrrolopyrimidinones as Potential Antitumor Agents. 1. Synthesis and Structure-Activity Relationships. Journal of Medicinal Chemistry. 2008;51:487-501.
Wade et al., Targeting Mdm2 and Mdmx in Cancer Therapy: Better Living through Medicinal Chemistry? Mol. Cancer Res. 2009;7:1-11.
Wang et al., Benzimidazole-2-one: A novel anchoring principle for antagonizing p53-Mdm2. Bioorganic & Medicinal Chemistry. 2013;21:3982-95.
Westphal The formation of pyrrolo[3,4-c]pyrazoles. Journal for Practical Chemistry. 1969;311:379-84.
Gein et al, "Synthesis and analgesic activity of 5-aryl-4-heteroyl-3-hydroxy-1-(2-thiazolyl)-3-pyrrolin-2-ones and their derivatives" Perm State Pharmaceutical Academy, Perm, 614990, Russia; Pharmaceutical Chemistry Journal (2014), 47(10),539-543.

PYRAZOLO-PYRROLIDIN-4-ONE DERIVATIVES AND THEIR USE IN THE TREATMENT OF DISEASE

This application is a U.S. National Phase filing of International Application No. PCT/IB2014/061743 filed 27 May 2014, which claims priority to EP Application No. 13169448.1 filed 28 May 2013, the contents of which are incorporated herein by reference in their entirety.

FIELD OF THE INVENTION

The invention provides pyrazolo-pyrrolidin-4-one derivatives and their use as BET inhibitors, for the treatment of conditions or diseases such as cancer.

BACKGROUND OF THE INVENTION

BET proteins are proteins encoded by either of the genes BRD2, BRD3, BRD4, or BRDT. Each of these proteins bears two N-terminal bromodomains. Bromodomains comprise of a conserved ~110 amino acid segment found in at least 42 diverse proteins that specifically interact with acetylated lysines that occur for example on histone tails (Filippakopoulos and Knapp, FEBS Letters, 586 (2012), 2692-2704). Histones are a constituent part of chromatin and their covalent modifications including lysine acetylation regulate gene transcription. Bromodomains are thus believed to regulate transcription by recruiting proteins to genes that are marked with specific patterns of lysine acetylation.

Several published reports have linked the BET protein family to diseases including cancer, metabolic disease and inflammation. Oncogenic fusions of BRD4 or BRD3 and the Nuclear protein in Testis (NUT) gene caused by chromosomal translocations are underlying an aggressive cancer named NUT midline carcinoma (French et al., J Clin Oncol, 22 (2004), 4135-9; French et al., J Clin Pathol, 63 (2008), 492-6). The BRD3/4 bromodomains are preserved in these fusion proteins, and their inhibition either by knockdown or with the selective BET bromodomain inhibitor JQ1 leads to death and/or differentiation of these cancer cells both in vitro and in animal tumour models (Filippakopoulos et al., Nature, 468 (2010), 1067-73). JQ1 and several other selective BET inhibitors have been shown to bind to BET bromodomains and thereby prevent acetyl-lysine binding, which prevents BET proteins from interacting with chromatin and thereby regulating transcription. BRD4 was also identified from an RNAi screen as a target in acute myeloid leukemia (AML) (Zuber et al., Nature, 478 (2011), 524-8). This finding was validated in vitro and in vivo using the BET inhibitor JQ1 and another selective BET inhibitor named I-BET151 that is chemically unrelated to JQ1 (Dawson et al., Nature, 478 (2011), 529-33). These and other studies showed that BET inhibitors have broad anti-cancer activity in acute leukemias, multiple myeloma and other hematological malignancies. In several cancer models an acute downregulation of the oncogenic transcription factor Myc upon BET inhibition has been observed (Delmore et al., Cell, 146 (2011), 904-17; Mertz et al., Proc Natl Acad Sci USA, 108 (2011), 16669-74). More recent studies suggest that the therapeutic potential of BET inhibitors extends to other cancer indications, for example lung and brain cancer.

Another BET inhibitor named I-BET762 that is closely related to JQ1 in chemical structure and the manner in which it binds to BET bromodomains, was reported to modulate expression of key inflammatory genes and thereby protect against endotoxic shock and bacteria-induced sepsis in mouse models (Nicodeme et al., Nature, 468 (2010), 1119-23). This body of data has been used to support the clinical evaluation of the BET inhibitor RVX-208 in clinical trials in patients suffering from atherosclerosis, coronary artery disease, dyslipidemia, diabetes, and other cardiovascular diseases (McNeill, Curr Opin Investig Drugs, 3 (2010), 357-64 and www.clinicaltrials.gov), Both RVX-208 and I-BET762 have been shown to upregulate Apolipoprotein A-I, which is critically involved in reducing the tissue levels of cholesterol. Finally, BET proteins have been linked to propagation and transcription regulation of several viruses, and therefore it is believed that BET inhibitors could have anti-viral activity (Weidner-Glunde, Frontiers in Bioscience 15 (2010), 537-549).

In summary, inhibitors of BET bromodomains have therapeutic potential in several human diseases.

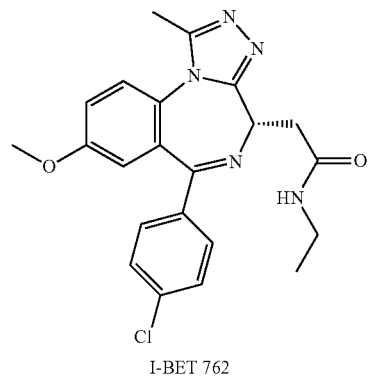
I-BET 762

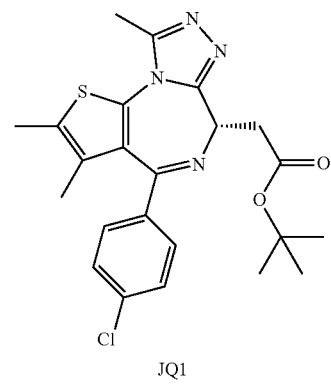
JQ1

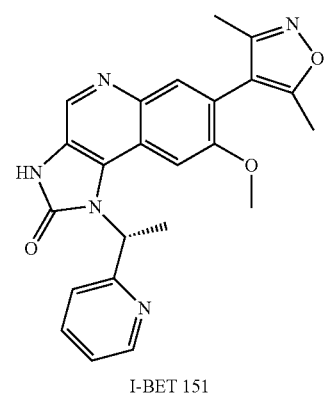
I-BET 151

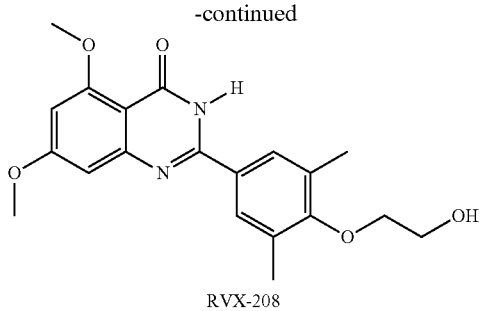

RVX-208

SUMMARY OF THE INVENTION

There remains a need for new treatments and therapies for the treatment of cancer. The invention provides compounds as BET inhibitors, pharmaceutically acceptable salts thereof, pharmaceutical compositions thereof and combinations thereof. The invention further provides methods of treating, preventing or ameliorating cancer, comprising administering to a subject in need thereof an effective amount of a BET inhibitor.

Various embodiments of the invention are described herein. Particularly interesting compounds of the invention have good potency in the biological assays described herein. In another aspect they should have a favourable safety profile. In another aspect, they should possess favourable pharmacokinetic properties.

According to a first aspect of the invention, Embodiment 1, there is provided a compound of formula (I) or a salt thereof,

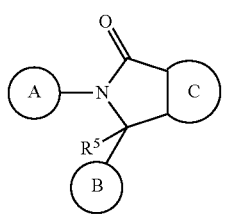
(I)

wherein
A is

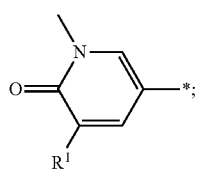

B is

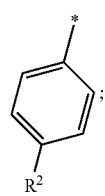

C is selected from:

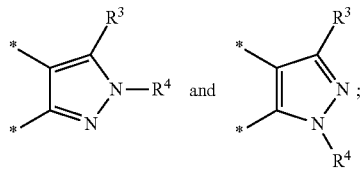

$R^1$ is selected from methyl and chloro;
$R^2$ is selected from chloro and fluoro;
$R^3$ is selected from methyl and cyclopropyl; and $R^4$ is selected from H; $(C_1-C_4)$alkyl optionally substituted by —OH or —O—$(C_1-C_4)$alkyl; cyclopropyl;

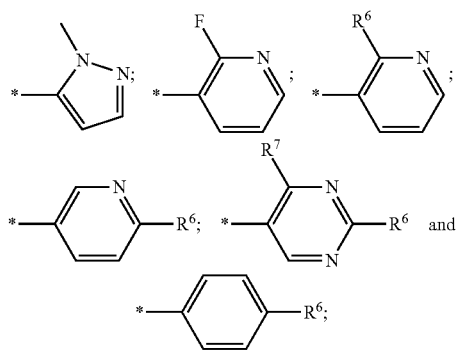

or
$R^3$ is

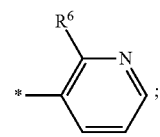

and $R^4$ is selected from H; $(C_1-C_4)$alkyl optionally substituted by —OH or —O—$(C_1-C_4)$alkyl; and cyclopropyl;
$R^5$ is H;
$R^6$ is —O—$(C_1-C_4)$alkyl;
$R^7$ is selected from H and methoxy;
and * indicates the point of attachment to the remainder of the molecule.

In another embodiment, the invention provides a pharmaceutical composition comprising a therapeutically effective amount of a compound according to the definition of formula (I), or a salt thereof, or subformulae thereof and one or more pharmaceutically acceptable carriers.

In another embodiment, the invention provides a combination, in particular a pharmaceutical combination, comprising a therapeutically effective amount of the compound according to the definition of formula (I), or a salt thereof, or subformulae thereof and one or more therapeutically active agents.

DETAILED DESCRIPTION

Described below are a number of embodiments (E) of the first aspect of the invention, where for convenience Embodiment 1 is identical thereto.

Unless specified otherwise, the term "compounds of the present invention" refers to compounds of formula (I) and subformulae thereof, and salts thereof, as well as all stereoisomers (including diastereoisomers and enantiomers), rotamers, tautomers and isotopically labeled compounds (including deuterium substitutions), as well as inherently formed moieties.

Unless specified otherwise, the term "compounds of the present invention" refers to compounds of formula (I) and subformulae thereof, and salts thereof, as well as all stereoisomers (including diastereoisomers and enantiomers), rotamers, tautomers and isotopically labeled compounds (including deuterium substitutions), as well as inherently formed moieties.

As used herein, the term "$C_{1-4}$alkyl" refers to a fully saturated branched or unbranched hydrocarbon moiety having 1 to 4 carbon atoms. Representative examples of $C_{1-4}$alkyl include methyl, ethyl, n-propyl, iso-propyl, n-butyl, sec-butyl, iso-butyl and tert-butyl.

Various embodiments of the invention are described herein. It will be recognized that features specified in each embodiment may be combined with other specified features to provide further embodiments of the present invention.

The invention therefore provides a compound of the formula (I) as described hereinabove as Embodiment 1.

Embodiment 2. A compound of formula (I), or a salt thereof, according to Embodiment 1, which is of the formula (Ia):

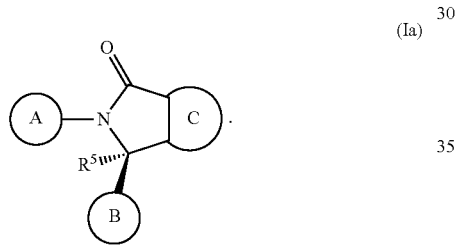

(Ia)

Embodiment 3. A compound of formula (I), or a pharmaceutically acceptable salt thereof, according to Embodiment 1 or 2, wherein the compound is of the formula (II) or (IIa):

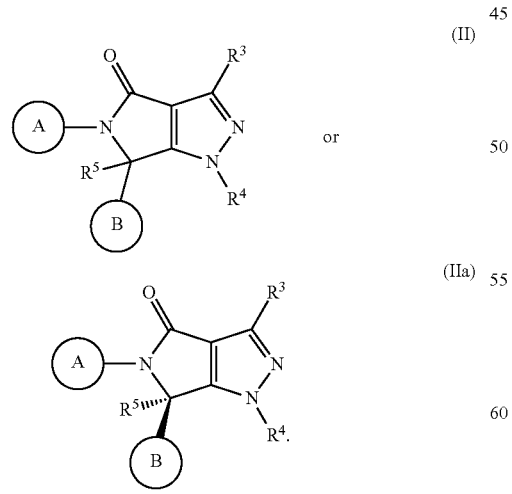

(II)

or (IIa)

Embodiment 4. A compound of formula (I), or a pharmaceutically acceptable salt thereof, according to Embodiment 1 or 2, wherein the compound is of the formula (III) or (IIIa):

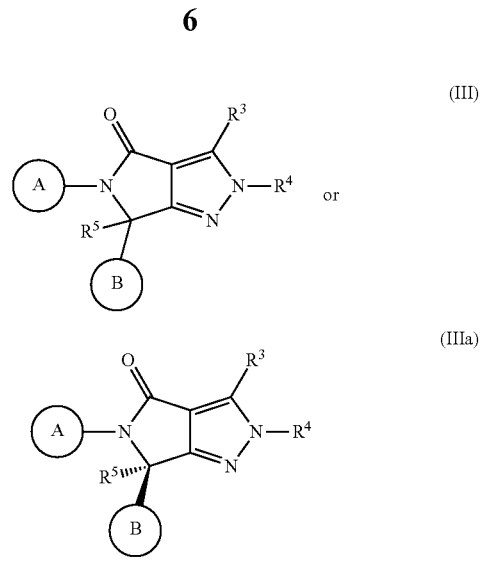

(III)

or (IIIa)

Embodiment 4. A compound of formula (I), or a salt thereof, according to any preceding Embodiment, wherein $R^2$ is chloro.

Embodiment 5. A compound of formula (I), or a salt thereof, according to any preceding Embodiment, wherein $R^3$ is selected from methyl, cyclopropyl, and

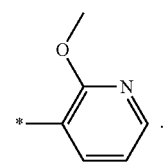

.

Embodiment 6. A compound of formula (I), or a salt thereof, according to any preceding Embodiment, wherein $R^4$ is selected from methyl, ethyl, isopropyl, —CH$_2$CH$_2$OH, —CH$_2$CH$_2$OCH$_3$, cyclopropyl,

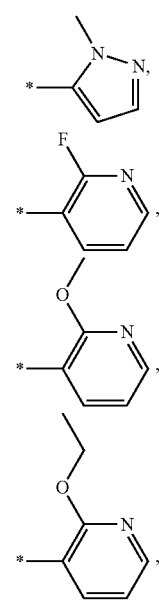

,

-continued

[chemical structures: *-pyridine-OMe, *-O-pyrimidine-OMe, *-pyrimidine-OMe, and *-phenyl-OMe]

or R⁴ is H.

Embodiment 7. A compound of formula (I) or a salt thereof, according to any one of Embodiments 1 or 3 to 6, wherein the compound is present as the racemate of the 2 enantiomeric forms (Ia) and (Ib) disclosed herein.

Embodiment 8. A compound of formula (I), or a salt thereof, according to Embodiment 1, selected from:

Example 1 6-(4-chlorophenyl)-3-cyclopropyl-5-(1,5-dimethyl-6-oxo-1,6-dihydropyridin-3-yl)-1-methyl-5,6-dihydropyrrolo[3,4-c]pyrazol-4(1H)-one;

Example 2: (R)-6-(4-chlorophenyl)-3-cyclopropyl-5-(3,8-dimethyl-[1,2,4]triazolo[4,3-a]pyridin-6-yl)-1-methyl-5,6-dihydropyrrolo[3,4-c]pyrazol-4(1H)-one;

Example 3: 6-(4-chlorophenyl)-3-cyclopropyl-5-(1,5-dimethyl-6-oxo-1,6-dihydropyridin-3-yl)-1-(2-hydroxyethyl)-5,6-dihydropyrrolo[3,4-c]pyrazol-4(1H)-one;

Example 4: 6-(4-chlorophenyl)-3-cyclopropyl-5-(1,5-dimethyl-6-oxo-1,6-dihydropyridin-3-yl)-1-(2-methoxyethyl)-5,6-dihydropyrrolo[3,4-c]pyrazol-4(1H)-one;

Example 5: 6-(4-chlorophenyl)-3-cyclopropyl-5-(1,5-dimethyl-6-oxo-1,6-dihydropyridin-3-yl)-1-(1-methyl-1H-pyrazol-5-yl)-5,6-dihydropyrrolo[3,4-c]pyrazol-4(1H)-one;

Example 6: 5-(5-chloro-1-methyl-6-oxo-1,6-dihydropyridin-3-yl)-6-(4-chlorophenyl)-3-methyl-5,6-dihydropyrrolo[3,4-c]pyrazol-4(2H)-one;

Example 7a: 5-(5-chloro-1-methyl-6-oxo-1,6-dihydropyridin-3-yl)-6-(4-chlorophenyl)-1-(2-methoxypyridin-3-yl)-3-methyl-5,6-dihydropyrrolo[3,4-c]pyrazol-4(1H)-one;

Example 7b: 5-(5-chloro-1-methyl-6-oxo-1,6-dihydropyridin-3-yl)-6-(4-chlorophenyl)-2-(2-methoxypyridin-3-yl)-3-methyl-5,6-dihydropyrrolo[3,4-c]pyrazol-4(2H)-one;

Example 8a: 5-(5-chloro-1-methyl-6-oxo-1,6-dihydropyridin-3-yl)-6-(4-chlorophenyl)-1-(2-methoxypyrimidin-5-yl)-3-methyl-5,6-dihydropyrrolo[3,4-c]pyrazol-4(1H)-one;

Example 8b: 5-(5-chloro-1-methyl-6-oxo-1,6-dihydropyridin-3-yl)-6-(4-chlorophenyl)-2-(2-methoxypyrimidin-5-yl)-3-methyl-5,6-dihydropyrrolo[3,4-c]pyrazol-4(2H)-one;

Example 9: 6-(4-chlorophenyl)-5-(1,5-dimethyl-6-oxo-1,6-dihydropyridin-3-yl)-3-methyl-5,6-dihydropyrrolo[3,4-c]pyrazol-4(2H)-one;

Example 10: 6-(4-chlorophenyl)-5-(1,5-dimethyl-6-oxo-1,6-dihydropyridin-3-yl)-1,3-dimethyl-5,6-dihydropyrrolo[3,4-c]pyrazol-4(1H)-one;

Example 11: 6-(4-chlorophenyl)-1-cyclopropyl-5-(1,5-dimethyl-6-oxo-1,6-dihydropyridin-3-yl)-3-methyl-5,6-dihydropyrrolo[3,4-c]pyrazol-4(1H)-one;

Example 12: 6-(4-chlorophenyl)-5-(1,5-dimethyl-6-oxo-1,6-dihydropyridin-3-yl)-1-isopropyl-3-methyl-5,6-dihydropyrrolo[3,4-c]pyrazol-4(1H)-one;

Example 13: 6-(4-chlorophenyl)-5-(1,5-dimethyl-6-oxo-1,6-dihydropyridin-3-yl)-1-(4-methoxyphenyl)-3-methyl-5,6-dihydropyrrolo[3,4-c]pyrazol-4(1H)-one;

Example 14: 6-(4-chlorophenyl)-2-(2,4-dimethoxypyrimidin-5-yl)-5-(1,5-dimethyl-6-oxo-1,6-dihydropyridin-3-yl)-3-methyl-5,6-dihydropyrrolo[3,4-c]pyrazol-4(2H)-one;

Example 15: 6-(4-chlorophenyl)-5-(1,5-dimethyl-6-oxo-1,6-dihydropyridin-3-yl)-3-(2-methoxypyridin-3-yl)-1-methyl-5,6-dihydropyrrolo[3,4-c]pyrazol-4(1H)-one;

Example 16: (R)-6-(4-chlorophenyl)-5-(1,5-dimethyl-6-oxo-1,6-dihydropyridin-3-yl)-3-(2-methoxypyridin-3-yl)-1-methyl-5,6-dihydropyrrolo[3,4-c]pyrazol-4(1H)-one;

Example 17a: 6-(4-chlorophenyl)-5-(1,5-dimethyl-6-oxo-1,6-dihydropyridin-3-yl)-1-(2-methoxypyridin-3-yl)-3-methyl-5,6-dihydropyrrolo[3,4-c]pyrazol-4(1H)-one;

Example 17b: 6-(4-chlorophenyl)-5-(1,5-dimethyl-6-oxo-1,6-dihydropyridin-3-yl)-2-(2-methoxypyridin-3-yl)-3-methyl-5,6-dihydropyrrolo[3,4-c]pyrazol-4(2H)-one;

Example 18a: 6-(4-chlorophenyl)-5-(1,5-dimethyl-6-oxo-1,6-dihydropyridin-3-yl)-1-(2-ethoxypyridin-3-yl)-3-methyl-5,6-dihydropyrrolo[3,4-c]pyrazol-4(1H)-one;

Example 18b: 6-(4-chlorophenyl)-5-(1,5-dimethyl-6-oxo-1,6-dihydropyridin-3-yl)-2-(2-ethoxypyridin-3-yl)-3-methyl-5,6-dihydropyrrolo[3,4-c]pyrazol-4(2H)-one;

Example 19: 6-(4-chlorophenyl)-5-(1,5-dimethyl-6-oxo-1,6-dihydropyridin-3-yl)-1-(2-fluoropyridin-3-yl)-3-methyl-5,6-dihydropyrrolo[3,4-c]pyrazol-4(1H)-one;

Example 20a: 6-(4-chlorophenyl)-5-(1,5-dimethyl-6-oxo-1,6-dihydropyridin-3-yl)-2-(6-methoxypyridin-3-yl)-3-methyl-5,6-dihydropyrrolo[3,4-c]pyrazol-4(2H)-one;

Example 20b: 6-(4-chlorophenyl)-5-(1,5-dimethyl-6-oxo-1,6-dihydropyridin-3-yl)-1-(6-methoxypyridin-3-yl)-3-methyl-5,6-dihydropyrrolo[3,4-c]pyrazol-4(1H)-one;

Example 21a: 6-(4-chlorophenyl)-5-(1,5-dimethyl-6-oxo-1,6-dihydropyridin-3-yl)-1-(2-methoxypyrimidin-5-yl)-3-methyl-5,6-dihydropyrrolo[3,4-c]pyrazol-4(1H)-one;

Example 21b: 6-(4-chlorophenyl)-5-(1,5-dimethyl-6-oxo-1,6-dihydropyridin-3-yl)-2-(2-methoxypyrimidin-5-yl)-3-methyl-5,6-dihydropyrrolo[3,4-c]pyrazol-4(2H)-one;

Example 22: (R)-6-(4-chlorophenyl)-3-cyclopropyl-5-(1,5-dimethyl-6-oxo-1,6-dihydropyridin-3-yl)-1-(1-methyl-1H-pyrazol-5-yl)-5,6-dihydropyrrolo[3,4-c]pyrazol-4(1H)-one;

Example 23: 6-(4-chlorophenyl)-3-cyclopropyl-5-(1,5-dimethyl-6-oxo-1,6-dihydropyridin-3-yl)-5,6-dihydropyrrolo[3,4-c]pyrazol-4(1H)-one;

Example 24: (R)-6-(4-chlorophenyl)-3-cyclopropyl-5-(1,5-dimethyl-6-oxo-1,6-dihydropyridin-3-yl)-5,6-dihydropyrrolo[3,4-c]pyrazol-4(1H)-one;

Example 25: (R)-6-(4-chlorophenyl)-5-(1,5-dimethyl-6-oxo-1,6-dihydropyridin-3-yl)-1-(2-methoxypyridin-3-yl)-3-methyl-5,6-dihydropyrrolo[3,4-c]pyrazol-4(1H)-one;

Example 26: (R)-6-(4-chlorophenyl)-5-(1,5-dimethyl-6-oxo-1,6-dihydropyridin-3-yl)-2-(2-methoxypyridin-3-yl)-3-methyl-5,6-dihydropyrrolo[3,4-c]pyrazol-4(2H)-one;

Example 27: (R)-6-(4-chlorophenyl)-5-(1,5-dimethyl-6-oxo-1,6-dihydropyridin-3-yl)-3-methyl-5,6-dihydropyrrolo[3,4-c]pyrazol-4(2H)-one; and Example 28: (R)-5-(5-chloro-1-methyl-6-oxo-1,6-dihydropyridin-3-yl)-6-(4-chlorophenyl)-3-methyl-5,6-dihydropyrrolo[3,4-c]pyrazol-4(2H)-one.

Embodiment 9. A compound of formula (I), or a salt thereof, according to Embodiment 1, selected from:

Example 2: (R)-6-(4-chlorophenyl)-3-cyclopropyl-5-(3,8-dimethyl-[1,2,4]triazolo[4,3-a]pyridin-6-yl)-1-methyl-5,6-dihydropyrrolo[3,4-c]pyrazol-4(1H)-one;

Example 11: 6-(4-chlorophenyl)-1-cyclopropyl-5-(1,5-dimethyl-6-oxo-1,6-dihydropyridin-3-yl)-3-methyl-5,6-dihydropyrrolo[3,4-c]pyrazol-4(1H)-one;

Example 16: (R)-6-(4-chlorophenyl)-5-(1,5-dimethyl-6-oxo-1,6-dihydropyridin-3-yl)-3-(2-methoxypyridin-3-yl)-1-methyl-5,6-dihydropyrrolo[3,4-c]pyrazol-4(1H)-one;

Example 17b: 6-(4-chlorophenyl)-5-(1,5-dimethyl-6-oxo-1,6-dihydropyridin-3-yl)-2-(2-methoxypyridin-3-yl)-3-methyl-5,6-dihydropyrrolo[3,4-c]pyrazol-4(2H)-one;

Example 20a: 6-(4-chlorophenyl)-5-(1,5-dimethyl-6-oxo-1,6-dihydropyridin-3-yl)-2-(6-methoxypyridin-3-yl)-3-methyl-5,6-dihydropyrrolo[3,4-c]pyrazol-4(2H)-one;

Example 20b: 6-(4-chlorophenyl)-5-(1,5-dimethyl-6-oxo-1,6-dihydropyridin-3-yl)-1-(6-methoxypyridin-3-yl)-3-methyl-5,6-dihydropyrrolo[3,4-c]pyrazol-4(1H)-one;

Example 21a: 6-(4-chlorophenyl)-5-(1,5-dimethyl-6-oxo-1,6-dihydropyridin-3-yl)-1-(2-methoxypyrimidin-5-yl)-3-methyl-5,6-dihydropyrrolo[3,4-c]pyrazol-4(1H)-one;

Example 24: (R)-6-(4-chlorophenyl)-3-cyclopropyl-5-(1,5-dimethyl-6-oxo-1,6-dihydropyridin-3-yl)-5,6-dihydropyrrolo[3,4-c]pyrazol-4(1H)-one;

Example 25: (R)-6-(4-chlorophenyl)-5-(1,5-dimethyl-6-oxo-1,6-dihydropyridin-3-yl)-1-(2-methoxypyridin-3-yl)-3-methyl-5,6-dihydropyrrolo[3,4-c]pyrazol-4(1H)-one; and Example 26: (R)-6-(4-chlorophenyl)-5-(1,5-dimethyl-6-oxo-1,6-dihydropyridin-3-yl)-2-(2-methoxypyridin-3-yl)-3-methyl-5,6-dihydropyrrolo[3,4-c]pyrazol-4(2H)-one.

The present disclosure includes compounds of stereochemistry is as shown in formula (Ib):

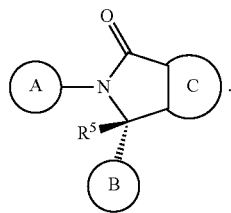

(Ib)

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

In another aspect, the present invention provides compounds of formula I in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F, $^{31}$P, $^{32}$P, $^{35}$S, $^{36}$Cl, $^{123}$I, $^{124}$I, $^{125}$I respectively. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by BET proteins, or (ii) associated with BET protein activity, or (iii) characterized by activity (normal or abnormal) of BET proteins; or (2) reduce or inhibit the activity of BET proteins; or (3) reduce or inhibit the expression of BET. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of BET proteins; or at least partially reducing or inhibiting the expression of BET proteins.

A "BET protein" is a protein encoded by either of the genes BRD2, BRD3, BRD4, or BRDT". Unless indicated otherwise "BET proteins" or "BET protein" are used herein in the singular and plural forms interchangeably, and the use of either is not limiting. Unless indicated otherwise "BET proteins" includes all, or any combination of, such encoded proteins.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Compositions:

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc. Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The compounds of formula I in free form or in pharmaceutically acceptable salt form, exhibit valuable pharmacological properties, e.g. BET protein modulating properties, e.g. as indicated in tests as provided in the next sections, and are therefore indicated for therapy or for use as research chemicals, e.g. as tool compounds.

Having regard to their activity as BET inhibitors, compounds of the formula (I) in free or pharmaceutically acceptable salt form, are useful in the treatment of conditions which are mediated by the activity of BET proteins, such as cancer, and/or that are responsive (meaning especially in a therapeutically beneficial way) to inhibition of a BET protein, most especially a disease or disorder as mentioned herein below.

Compounds of the invention are believed to be useful in the treatment of diseases or disorders such as cancer. In particular, such cancers include benign or malignant tumours, a soft tissue sarcoma or a sarcoma such as liposarcoma, rhabdomyosarcoma or bone cancer, e.g. osteosarcoma, a carcinoma, such as of the brain, kidney, liver, adrenal gland, bladder, breast, gastric, ovary, colon, rectum, prostate, pancreas, lung (including small cell lung cancer), vagina or thyroid, a glioblastoma, meningioma, glioma, mesothelioma, a neuroendocrine tumor such as neuroblastoma, a multiple myeloma, a gastrointestinal cancer, especially colon carcinoma or colorectal adenoma, a tumor of the head and neck, a melanoma, a prostate hyperplasia, a neoplasia, a neoplasia of epithelial character, a neoplasia originating from blood or bone marrow, a leukemia such as acute myeloid leukemia (AML) or acute lymphoblastic leukemia (ALL) or B-cell chronic lymphocytic leukemia, a lymphoma, such as of B- or T-cell origin, such as diffuse large B cell lymphoma (DLBCL), NUT midline carcinoma or any other neoplasia with chromosomal rearrangements of the BET genes, and metastases in other organs. In particular, compounds of the invention are believed to be useful in a cancer selected from a neoplasia originating from blood or bone marrow; a leukemia such as acute myeloid leukemia (AML) or acute lymphoblastic leukemia (ALL) or B-cell chronic lymphocytic leukemia; a lymphoma, such as of B- or T-cell origin, such as diffuse large B cell lymphoma (DLBCL); NUT midline carcinoma or any other neoplasia with chromosomal rearrangements of the BET genes, a neuroendocrine tumor such as neuroblastoma; a multiple myeloma; a lung cancer (including small cell lung cancer); and a colon cancer.

Compounds of the invention may also be of use in the treatment of atherosclerosis, coronary artery disease, dyslipidemia, diabetes, and other cardiovascular diseases, and/or as antiviral agents.

Thus, as a further embodiment, the present invention provides the use of a compound of formula (I) or a salt thereof, in therapy. In a further embodiment, the therapy is selected from a disease which may be treated by inhibition of BET proteins. In another embodiment, the disease is a cancer disease selected from the afore-mentioned list.

Thus, as a further embodiment, the present invention provides a compound of formula (I) or a salt thereof, for use in therapy. In a further embodiment, the therapy is selected from a disease which may be treated by inhibition of a BET protein. In another embodiment, the disease is a cancer disease selected from the afore-mentioned list.

In another embodiment, the invention provides a method of treating a disease which is treated by inhibition of a BET protein, comprising administration of a therapeutically acceptable amount of a compound of formula (I) or salt thereof. In a further embodiment, the disease is a cancer disease selected from the afore-mentioned list.

Thus, as a further embodiment, the present invention provides the use of a compound of formula (I) or salt thereof, for the manufacture of a medicament. In a further embodiment, the medicament is for treatment of a disease which may be treated by inhibition of a BET protein. In another embodiment, the disease is a cancer disease selected from the afore-mentioned list.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

Combinations

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by a BET protein. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by a BET protein, wherein the medicament is prepared for administration with another therapeutic agent. The invention also provides the use of another therapeutic agent for treating a disease or condition mediated by a BET protein, wherein the medicament is administered with a compound of formula (I).

The invention also provides a compound of formula (I) for use in a method of treating a disease or condition mediated by a BET protein, wherein the compound of formula (I) is prepared for administration with another therapeutic agent. The invention also provides another therapeutic agent for use in a method of treating a disease or condition mediated by a BET protein, wherein the other therapeutic agent is prepared for administration with a compound of formula (I). The invention also provides a compound of formula (I) for use in a method of treating a disease or condition mediated by a BET protein, wherein the compound of formula (I) is administered with another therapeutic agent. The invention also provides another therapeutic agent for use in a method of treating a disease or condition mediated by a BET protein, wherein the other therapeutic agent is administered with a compound of formula (I).

The invention also provides the use of a compound of formula (I) for treating a disease or condition mediated by a BET protein, wherein the patient has previously (e.g. within 24 hours) been treated with another therapeutic agent. The invention also provides the use of another therapeutic agent for treating a disease or condition mediated by a BET protein, wherein the patient has previously (e.g. within 24 hours) been treated with a compound of formula (I).

In one embodiment, the other therapeutic agent is an anticancer agent.

In a further embodiment, the other therapeutic agent is a modulator of a target in the field of epigenetics, such as an inhibitor of histone deacetylase (HDAC), or an inhibitor of histone methyltransferase (HMT).

Generic Schemes

Typically, the compounds of formula (I) can be prepared according to the Schemes provided infra.

Compounds of formula (I), wherein C is

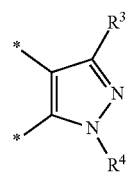

and $R^1$, $R^2$, $R^3$, $R^4$, $R^5$, $R^6$ and $R^7$ are as defined in Embodiment 1, may be prepared as described in Scheme 1.

Scheme 1

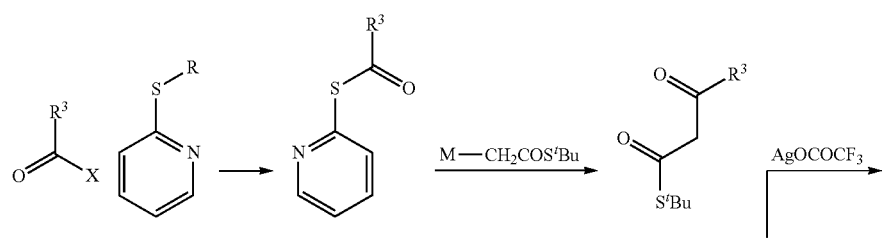

-continued

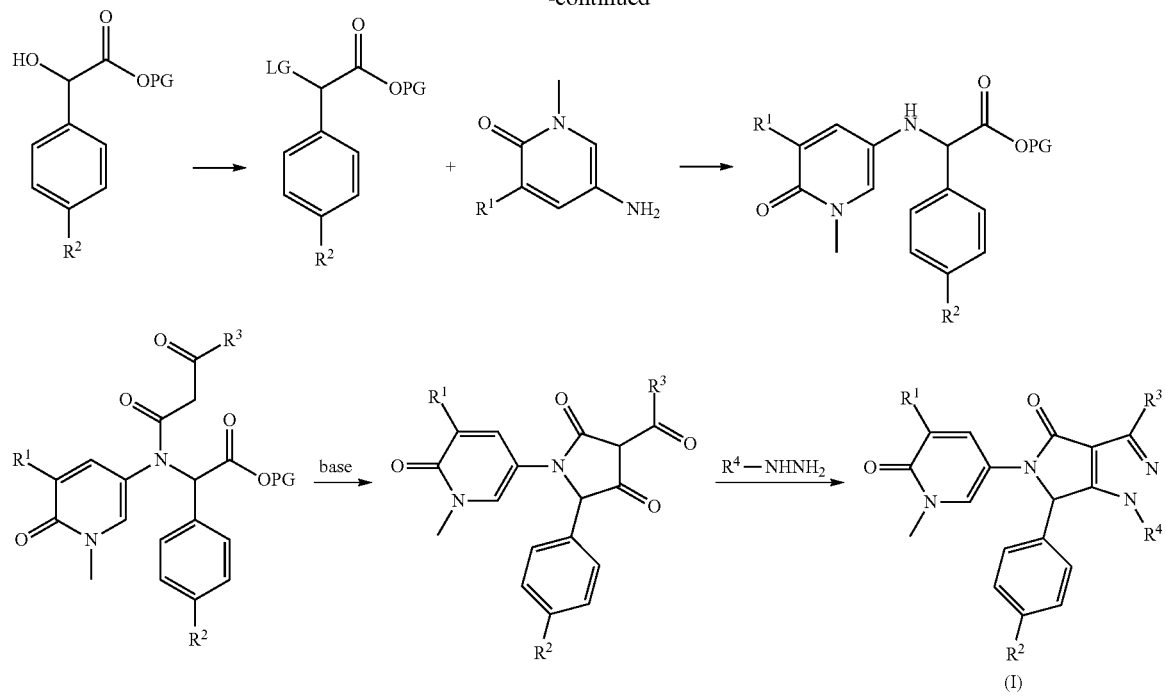

wherein
R is —H or —S-(pyridine-2-yl);
X is —OH or Cl;
M is a suitable metal, such as Li or Na;
LG is a suitable leaving group, such as mesylate; and
PG is a suitable acid protecting group, such as methyl.

Scheme 1 illustrates one method for preparing compounds of the invention (e.g. Examples 1-7 and 10-17). A carboxylic acid or acid chloride is converted with 1,2-di(pyridin-2-yl) disulfane or pyridine-2-thiol into the corresponding 2-thio-pyridine ester derivative, which can be reacted with S-tert-butyl ethanethioate in the presence of an appropriate strong base (LiHMDS, NaHMDS) to provide the corresponding beta-keto-thioester derivative. Conversion of the secondary alcohol of the corresponding 2-aryl-2-hydroxy-acetate derivative into a leaving group, for example with (a) methanesulfonyl chloride or methanesulfonic anhydride in the presence of an organic base such as pyridine (together with a catalytic amount of 4-dimethylaminopyridine) or triethylamine or (b) 1-chloro-N,N,2-trimethylpropenylamine, followed by reaction with the corresponding amine at temperatures between −20° C. and 50° C. results in the introduction of the 5-amino-1-methylpyridin-2(1H)-one moiety containing different $R^1$-substituents at C-3. The resulting secondary amine is reacted with a β-keto-thioester derivative in the presence of silver(I) trifluoroacetate at ambient temperature to provide the corresponding β-keto-thioamide derivative. Subsequent Claisen condensation to the cyclized beta-diketone can be effected under basic conditions (a) either with CsF in DMF at a temperature between 20° C. and 100° C. or (b) with sodium ethoxide in EtOH at elevated temperature. The pyrazolo-pyrrolidinone derivative is usually generated by condensation of the beta-diketone derivative with the corresponding $R^4$-containing hydrazine in a solvent such as methanol or ethanol at elevated temperature, preferably between 60-150° C. For the condensation of the beta-diketone derivative with aryl- and heteroaryl containing hydrazines, the final dehydration step to the pyrazolo-pyrrolidinone can be facilitated by addition of acetic acidic or a combination of acetic acid and sulfamic acid and at elevated temperature, preferably between 100-150° C. in a microwave oven.

Alternatively, compounds of formula (I), wherein C, $R^1$, $R^2$, $R^3$, $R^4$, $R^5$ and $R^6$ are as defined in Embodiment 1, may be prepared as described in Scheme 2.

Scheme 2

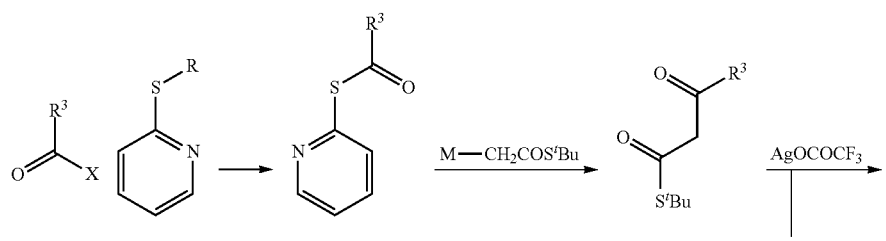

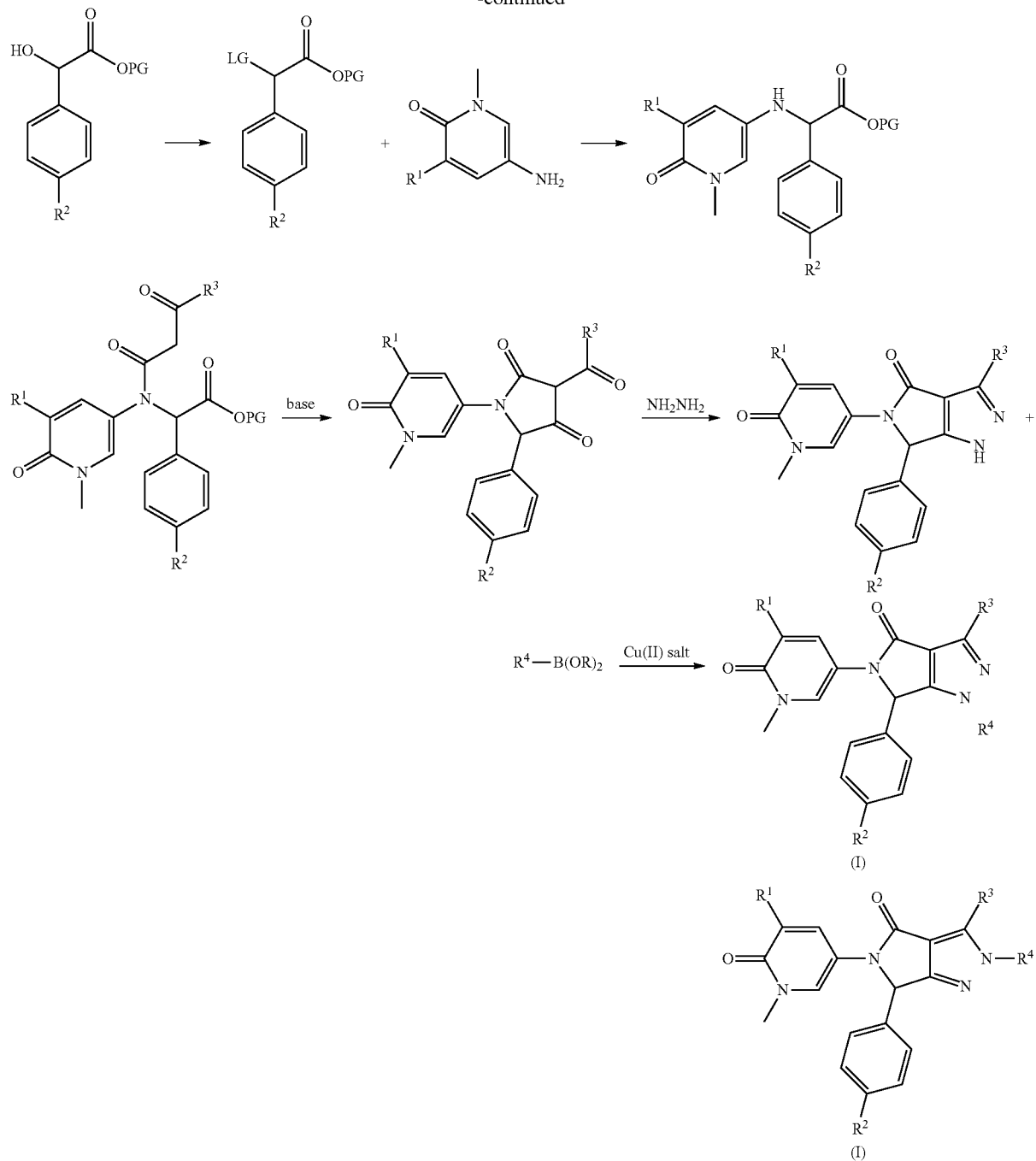

wherein X, M, LG and PG are as defined in Scheme 1.

Scheme 2 illustrates a modification of the method shown in Scheme 1 for preparing compounds of the invention (e.g. Examples 8-9 and 18-21). This method is similar to the one described in Scheme 1 except that the $R^4$-substituent is introduced by Chan-Lam coupling. The N-unsubstituted pyrazolo-pyrrolidinone derivative is treated with the $R^4$-containing boronic acid derivative and an appropriate Cu(II)-salt, such as Cu(OAc)$_2$, and pyridine in an appropriate solvent such as acetonitrile at elevated temperatures, preferable between 60-80° C.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material. Compounds of the invention and intermediates can also be converted into each other according to methods generally known to those skilled in the art.

Synthetic Methods

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

ABBREVIATIONS

ACN acetonitrile
$Ac_2O$ acetic acid anhydride
aq. aqueous
Ar argon
Boc tert-butoxycarbonyl
Brine saturated (at rt) sodium chloride solution
br. s. broad singlet
$CH_2Cl_2$ dichloromethane
$Cu(OAc)_2$ copper(II) acetate
d doublet
DIPEA diisopropyl ethyl amine
DMAP 4-dimethylaminopyridine
DMF N,N-dimethylformamide
DMSO dimethylsulfoxide
eq. equivalent
ESI-MS electrospray ionisation mass spectrometry
EtOAc ethyl acetate
EtOH ethanol
h hour(s)
$H_2O$ water
$K_2CO_3$ potassium carbonate
$K_3PO_4$ potassium phosphate
LC-MS liquid chromatography mass spectrometry
LiHMDS lithium hexamethyldisilazide
m multiplet
MeOH methanol
$MgSO_4$ magnesium sulfate
min minute(s)
mL milliliter(s)
MS mass spectrometry
$Ms_2O$ methanesulfonic anhydride
MW microwave
$NaHCO_3$ sodium bicarbonate
NaOH sodium hydroxide
$Na_2SO_4$ sodium sulfate
$NH_4Cl$ ammonium chloride
NMR nuclear magnetic resonance
ppm parts per million
$R_f$ ratio of fronts
rt (or RT) room temperature
s singlet
sat. saturated
SFC supercritical fluid chromatography
t triplet
$t_R$ time of retention
TFA trifluoroacetic acid
THF tetrahydrofuran
TurboGrignard iPrMgCl.LiCl
UPLC ultra performance liquid chromatography
UPLC Method:

UPLC 1: Column: Acquity UPLC HSS T3 C18, 1.7 μm 2.1×50 mm, Flow: 1.0 mL/min. Column temperature: 30° C. Gradient: 5% to 100% B in 1.5 min, 100% B for 1 min, A=water+0.1% TFA, B=ACN+0.1% TFA
LC-MS Method:
LC-MS 1:
Column: Waters Acquity HSS T3, 1.8 μm, 2.1×50 mm, oven at 60° C. Flow: 1.0 mL/min. Gradient: 5% to 98% B in 1.40 min, then 98% B for 0.40 min, 98% to 5% B in 0.10 min, 5% B for 0.10 min; A=water+0.05% formic acid+3.75 mM ammonium acetate, B=ACN+0.04% formic acid. Detection UV/VIS (DAD), ESI (+/−). Mass spectrometer range: 100-1200 Da.

EXAMPLE 1

6-(4-chlorophenyl)-3-cyclopropyl-5-(1,5-dimethyl-6-oxo-1,6-dihydropyridin-3-yl)-1-methyl-5,6-dihydropyrrolo[3,4-c]pyrazol-4(1H)-one

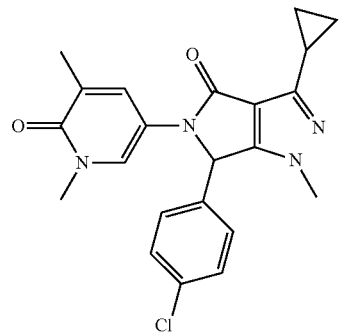 [SMILES: CNC1=C(C(=N)C2CC2)C(=O)N(c2cc(C)c(=O)n(C)c2)C1c1ccc(Cl)cc1]

To a solution of 5-(4-chlorophenyl)-3-(cyclopropanecarbonyl)-1-(1,5-dimethyl-6-oxo-1,6-dihydropyridin-3-yl)pyrrolidine-2,4-dione (160 mg, 0.4 mmol) in MeOH (1.5 mL) was added methylhydrazine (38 mg, 0.8 mmol) and the reaction mixture was stirred in the MW for 2.5 h at 110° C. The reaction mixture was concentrated and the residual oil was purified by silica gel column chromatography (hexane/EtOAc/MeOH 75:25:5 to 0:100:10) to afford the title product (110 mg, 67% yield) as a light yellow foam. $t_R$: 0.881 min (UPLC 1); $t_R$: 0.89 min (LC-MS 1); ESI-MS: 409/411 $[M+H]^+$ (LC-MS 1); $^1H$ NMR (400 MHz, DMSO-$d_6$) δ ppm 0.94-1.12 (m, 4 H) 1.93 (s, 3 H) 1.98 (m, 1 H) 3.35 (s, 3 H) 3.43 (s, 3 H) 6.23 (s, 1 H) 7.28-7.34 (m, 3 H) 7.44 (d, J=8.4 Hz, 2 H) 7.63 (d, J=2.7 Hz, 1 H).

Step 1.1: ethyl 2-(4-chlorophenyl)-2-((1,5-dimethyl-6-oxo-1,6-dihydropyridin-3-yl)amino)acetate

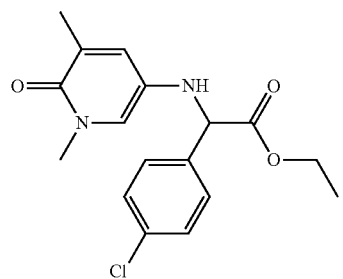 [SMILES: CCOC(=O)C(Nc1cc(C)c(=O)n(C)c1)c1ccc(Cl)cc1]

To a solution of ethyl 2-(4-chlorophenyl)-2-hydroxyacetate (3.22 g, 15 mmol) and NEt₃ (10.45 mL, 75.0 mmol) in CH₂Cl₂ (60 mL) was added at 0° C. Ms₂O (5.23 g, 30.0 mmol). The resulting reaction mixture was stirred for 0.5 h at 0° C. To the reaction mixture was added 5-amino-1,3-dimethylpyridin-2(1H)-one (1.946 g, 12.00 mmol) and the reaction mixture was allowed to warm to RT. After heating for 16 h at 40-45° C., the reaction mixture was added to sat. NaHCO₃ solution and EtOAc and the product was extracted with EtOAc. Combined extracts were washed with a small amount of brine, dried over MgSO₄, filtered and concentrated. The crude product was purified by silica gel column chromatography (hexane/EtOAc/MeOH 80:20:2 to 0:100:10) to afford the title product (3.0 g, 59% yield) as a brown foam. $t_R$: 0.939 min (UPLC 1); $t_R$: 0.93 min (LC-MS 1); ESI-MS: 335/337 [M+H]⁺ (LC-MS 1); $R_f$=0.30 (EtOAc/MeOH 9:1); ¹H NMR (400 MHz, CDCl₃) δ ppm 1.14 (t, J=7.1 Hz, 3 H) 2.05 (s, 3 H) 3.31 (s, 3 H) 4.01-4.23 (m, 2 H) 4.63 (m, 1 H) 6.11 (br. s., 1 H) 6.88 (br. s., 1 H) 7.24-7.35 (m, 4 H).

Step 1.2: ethyl 2-(4-chlorophenyl)-2-(3-cyclopropyl-N-(1,5-dimethyl-6-oxo-1,6-dihydropyridin-3-yl)-3-oxopropanamido)acetate To a solution of ethyl 2-(4-chlorophenyl)-2-((3,8-dimethyl-[1,2,4]triazolo[4,3-a]pyridin-6-yl)-amino)acetate (Step 1.1) (1.005 g, 3.0 mmol) and S-tert-butyl 3-cyclopropyl-3-oxopropanethioate (Step 1.5) (785 mg, 3.9 mmol) in THF (25 mL) was added silver trifluoroacetate (861 mg, 3.9 mmol) at RT. The resulting dark brown solution was stirred for 0.5 h at RT. The reaction mixture was filtered over Celite, the filtrate concentrated and the resulting crude product was purified by silica gel column chromatography (hexane/EtOAc 90:10 to 0:100) to afford the title product (1.13 g, 82% yield) as a reddish foam. $R_f$=0.18 (EtOAc); $t_R$: 0.955 min (UPLC 1); $t_R$: 0.94 min (LC-MS 1); ESI-MS: 445/447 [M+H]⁺ (LC-MS 1).

Step 1.3: 5-(4-chlorophenyl)-3-(cyclopropanecarbonyl)-1-(1,5-dimethyl-6-oxo-1,6-dihydropyridin-3-yl)pyrrolidine-2,4-dione

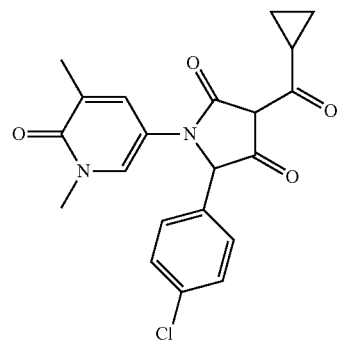 [SMILES: Cc1cc(N2C(=O)C(C(=O)C3CC3)C(=O)C2c2ccc(Cl)cc2)cn(C)c1=O]

To a solution of ethyl 2-(4-chlorophenyl)-2-(3-cyclopropyl-N-(3,8-dimethyl-[1,2,4]triazolo[4,3-a]pyridin-6-yl)-3-oxopropanamido)acetate (Step 1.2) (1.0 g, 2.25 mmol) in DMF (10 mL) was added under Ar at RT CsF (0.7 g, 2 mmol) and the resulting dark brown solution was stirred for 16 h at 60° C. The reaction mixture was concentrated and to the residue was added cold 1N H₂SO₄ and the product was extracted with EtOAc. Combined extracts were washed with brine, dried over MgSO₄, filtered, concentrated and dried at 60° C. to provide the title product (625 mg, 70%) as a yellow foam. $t_R$: 1.083 min (UPLC 1); $t_R$: 0.86 min (LC-MS 1); ESI-MS: 399/401 [M+H]⁺ (LC-MS 1).

Step 1.4: S-pyridin-2-yl cyclopropanecarbothioate

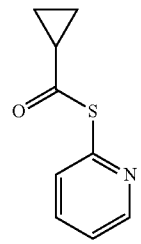 [SMILES: O=C(Sc1ccccn1)C1CC1]

To a solution of pyridine-2-thiol (29.2 g, 260 mmol) in THF (260 mL) was added under Ar the cyclopropanecarbonyl chloride (27.7 g, 260 mmol) at RT and the reaction mixture was stirred at 25° C. for 0.5 h. The precipitated HCl-salt was filtered off and washed with Et₂O-hexane 1:4 and hexane. The light yellow precipitate was added to sat. NaHCO₃ solution and EtOAc and the product was extracted with EtOAc. Combined extracts were washed with brine, dried over MgSO₄, filtered and concentrated to provide the title compound (37.3 g, 80% yield) as a yellow oil. $t_R$: 0.79 min (LC-MS 1); ESI-MS: 180 [M+H]⁺ (LC-MS 1); ¹H NMR (400 MHz, CDCl₃) δ ppm 0.83-1.03 (m, 2 H) 1.09-1.28 (m, 2 H) 1.91-2.16 (m, 1 H) 7.10-7.28 (m, 1 H) 7.60-7.74 (m, 1 H) 8.55 (dd, J=4.8, 1.1 Hz, 1 H).

Step 1.5: S-tert-butyl 3-cyclopropyl-3-oxopropanethioate

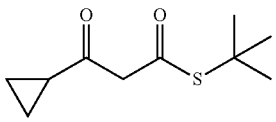

To a solution of S-pyridin-2-yl cyclopropanecarbothioate (Step 1.4) (16.5 g, 92 mmol) in THF (250 mL) was added under Ar a 1M LiHMDS solution in THF (229 mL, 229 mmol) at <−70° C. To the reaction mixture was added a solution of S-tert-butyl ethanethioate (14.0 mL, 96 mmol) in THF (30 mL) below −70° C. After stirring for 0.5 h at −78° C. the reaction mixture was slowly warmed up to −50° C. over a period of 1 h. After completion, the reaction mixture was added to 300 mL cold 1N $H_2SO_4$ and ice and the product was extracted with EtOAc. Combined extracts were washed with brine, dried over $MgSO_4$, filtered and concentrated. The crude oil was redissolved in $Et_2O$, kept at 0° C. for 14 h, filtered through a short plug of silicagel and concentrated again to provide the title product (18.3 g, 95% yield) as a yellow oil. $t_R$: 1.089 min (UPLC 1); $t_R$: 1.06 min (LC-MS 1); ESI-MS: 201 [M+H]$^+$ (LC-MS 1); $R_f$=0.59 (EtOAc); $^1$H NMR (400 MHz, CDCl$_3$) δ ppm 0.80 (m, 2 H) 0.91-0.99 (m, 2 H) 1.33 (s, 9 H) 1.92 (m, 1 H) 3.53 (s, 2 H).

EXAMPLE 2

(R)-6-(4-chlorophenyl)-3-cyclopropyl-5-(3,8-dimethyl-[1,2,4]triazolo[4,3-a]pyridin-6-yl)-1-methyl-5,6-dihydropyrrolo[3,4-c]pyrazol-4(1H)-one

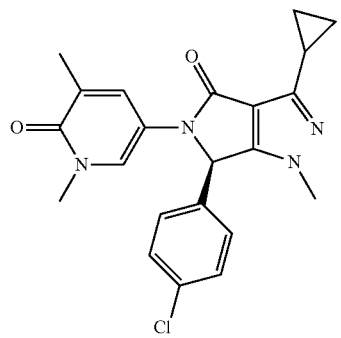 [SMILES: CNC1=C(C(=N)C2CC2)C(=O)N(c2cc(C)c(=O)n(C)c2)[C@@H]1c1ccc(Cl)cc1]

The title compound (33 mg, 45% yield) was obtained enantiomerically pure (>99% ee) as a white solid after chiral preparative chromatography (system: SFC-PicLab-Prep 100; column: Chiralpak IA 5 μm, 20×250 mm; mobile phase: heptane/ethanol/CH$_2$Cl$_2$ 60:20:20 (isocratic); flow: 10 mL/min; detection UV: 245 nm) of the racemic mixture of 6-(4-chlorophenyl)-3-cyclopropyl-5-(1,5-dimethyl-6-oxo-1,6-dihydropyridin-3-yl)-1-methyl-5,6-dihydropyrrolo[3,4-c]-pyrazol-4(1H)-one (Example 1) (72 mg, 0.176 mmol) and trituration of the resulting residue in Et$_2$O. $t_R$: 0.88 min (LC-MS 1); ESI-MS: 409/411 [M+H]$^+$ (LC-MS 1); $^1$H NMR (400 MHz, DMSO-d$_6$) δ ppm 0.94-1.12 (m, 4 H) 1.93 (s, 3 H) 1.98 (m, 1 H) 3.35 (s, 3H) 3.43 (s, 3 H) 6.23 (s, 1 H) 7.28-7.34 (m, 3 H) 7.44 (d, J=8.4 Hz, 2 H) 7.63 (d, J=2.7 Hz, 1 H).

EXAMPLE 3

6-(4-chlorophenyl)-3-cyclopropyl-5-(1,5-dimethyl-6-oxo-1,6-dihydropyridin-3-yl)-1-(2-hydroxyethyl)-5,6-dihydropyrrolo[3,4-c]pyrazol-4(1H)-one

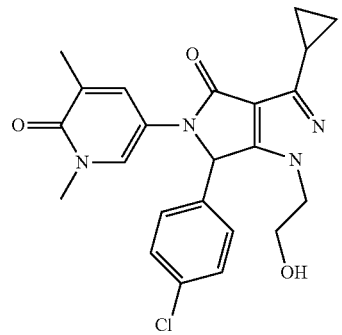 [SMILES: Cc1cc(N2C(=O)C(C(=N)C3CC3)=C(NCCO)C2c2ccc(Cl)cc2)cn(C)c1=O]

The title compound was prepared in analogy to the procedure described in Example 1 using 5-(4-chlorophenyl)-3-(cyclopropanecarbonyl)-1-(1,5-dimethyl-6-oxo-1,6-dihydropyridin-3-yl)pyrrolidine-2,4-dione (Step 1.3) and 2-hydrazinylethanol. $t_R$: 0.80 min (LC-MS 1); ESI-MS: 439/441 [M+H]$^+$ (LC-MS 1); $^1$H NMR (400 MHz, DMSO-d$_6$) δ ppm 0.95-1.15 (m, 4 H) 1.92 (s, 3 H) 1.95-2.04 (m, 1 H) 3.35 (s, 3 H) 3.42-3.61 (m, 4 H) 3.79-3.89 (m, 1 H) 4.97 (t, J=5.1 Hz, 1 H) 5.77 (s, 1 H) 6.18 (s, 1 H) 7.29 (d, J=8.4 Hz, 2 H) 7.35 (d, J=2.1 Hz, 1 H) 7.43 (d, J=8.4 Hz, 2 H) 7.67 (d, J=2.5 Hz, 1 H).

EXAMPLE 4

6-(4-chlorophenyl)-3-cyclopropyl-5-(1,5-dimethyl-6-oxo-1,6-dihydropyridin-3-yl)-1-(2-methoxyethyl)-5,6-dihydropyrrolo[3,4-c]pyrazol-4(1H)-one

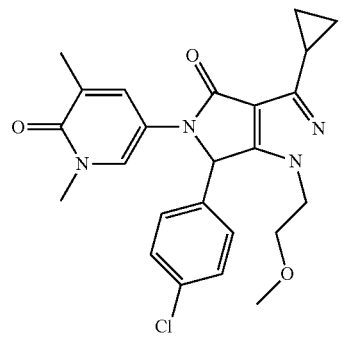 [SMILES: COCCNC1=C(C(=N)C2CC2)C(=O)N(c2cc(C)c(=O)n(C)c2)C1c1ccc(Cl)cc1]

The title compound was prepared in analogy to the procedure described in Example 1 using 5-(4-chlorophenyl)-3-(cyclopropanecarbonyl)-1-(1,5-dimethyl-6-oxo-1,6-dihydropyridin-3-yl)pyrrolidine-2,4-dione (Step 1.3) and (2-methoxyethyl)hydrazine. $t_R$: 0.93 min (LC-MS 1); ESI-MS: 475/477 [M+H]$^+$ (LC-MS 1); $^1$H NMR (400 MHz, DMSO-d$_6$) δ ppm 0.91-1.14 (m, 4 H) 1.92 (s, 3 H) 1.94-2.04 (m, 1 H) 3.11 (s, 3 H) 3.35 (s, 3 H) 3.41 (t, J=5.3 Hz, 2H) 3.67 (dt, J=14.4, 5.9 Hz, 1 H) 3.92 (dt, J=14.4, 4.7 Hz, 1H) 6.16 (s, 1H) 7.29 (d, J=8.3 Hz, 2H) 7.34 (d, J=1.9 Hz, 1H) 7.43 (d, J=8.4 Hz, 2H) 7.66 (d, J=2.5 Hz, 1H).

EXAMPLE 5

6-(4-chlorophenyl)-3-cyclopropyl-5-(1,5-dimethyl-6-oxo-1,6-dihydropyridin-3-yl)-1-(1-methyl-1H-pyrazol-5-yl)-5,6-dihydropyrrolo[3,4-c]pyrazol-4(1H)-one

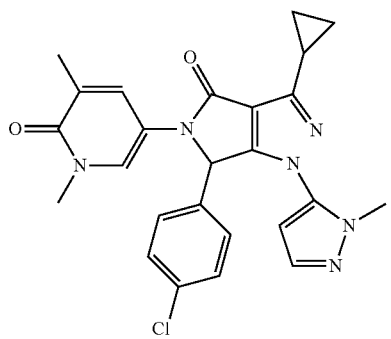 [SMILES: Cc1cc(N2C(=O)C(C(=N)C3CC3)=C(Nc3ccnn3C)C2c2ccc(Cl)cc2)cn(C)c1=O]

The title compound was prepared in analogy to the procedure described in Example 1, using 5-(4-chlorophenyl)-3-(cyclopropanecarbonyl)-1-(1,5-dimethyl-6-oxo-1,6-dihydropyridin-3-yl)pyrrolidine-2,4-dione (Step 1.3) and 5-hydrazinyl-1-methyl-1H-pyrazole. $t_R$: 0.93 min (LC-MS 1); ESI-MS: 475/477 [M+H]$^+$ (LC-MS 1); $^1$H NMR (400 MHz, DMSO-d$_6$) δ ppm 1.03-1.27 (m, 4 H) 1.93 (s, 3 H) 2.06-2.16 (m, 1 H) 3.35 (s, 3 H) 3.49 (s, 3 H) 5.77 (s, 1 H) 6.07 (d, J=2.1 Hz, 1 H) 6.37 (s, 1 H) 7.14 (d, J=8.2 Hz, 2 H) 7.32 (d, J=8.0 Hz, 2 H) 7.35-7.39 (m, 1 H) 7.44 (d, J=2.0 Hz, 1 H) 7.66 (d, J=2.5 Hz, 1 H).

EXAMPLE 6

5-(5-chloro-1-methyl-6-oxo-1,6-dihydropyridin-3-yl)-6-(4-chlorophenyl)-3-methyl-5,6-dihydropyrrolo[3,4-c]pyrazol-4(2H)-one

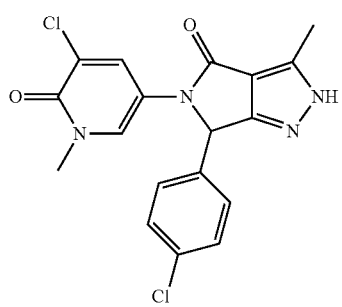 [SMILES: Cc1[nH]nc2c1C(=O)N(c1cc(Cl)c(=O)n(C)c1)C2c1ccc(Cl)cc1]

The title compound was prepared in analogy to the procedure described in Example 1 using 3-acetyl-1-(5-chloro-1-methyl-6-oxo-1,6-dihydropyridin-3-yl)-5-(4-chlorophenyl)pyrrolidine-2,4-dione (Step 6.3) and hydrazine hydrate. $R_f$=0.26 (CH$_2$Cl$_2$/MeOH 19:1); $t_R$: 0.73 min (LC-MS 1); ESI-MS: 389/391 [M+H]$^+$ (LC-MS 1); $^1$H NMR (400 MHz, DMSO-d$_6$) δ ppm 2.53 (s, 3H) 3.47 (s, 3H) 5.77 (s, 1H), 6.37 (s, 1H) 7.36 (d, J=8.2 Hz, 2 H) 7.43 (d, J=8.0 Hz, 2 H) 8.00 (s, 2H).

Step 6.1: ethyl 2-((5-chloro-1-methyl-6-oxo-1,6-dihydropyridin-3-yl)amino)-2-(4-chlorophenyl)-acetate

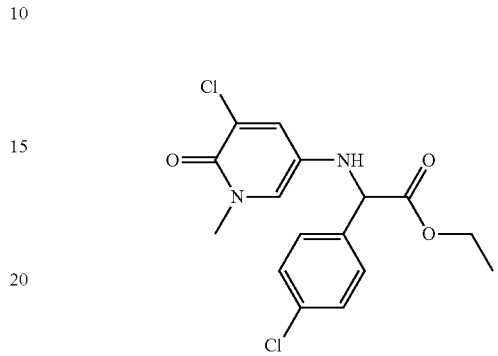

The title compound was prepared in analogy to the procedure described in Example 1 using ethyl 2-(4-chlorophenyl)-2-hydroxyacetate and 5-amino-3-chloro-1-methyl-pyridin-2(1H)-one. $R_f$=0.58 (EtOAc/MeOH 9:1); $t_R$: 0.96 min (LC-MS 1); ESI-MS: 353/355 [M−H]$^+$ (LC-MS 1); $^1$H NMR (400 MHz, CDCl$_3$) δ ppm 1.21 (t, J=7.2 Hz, 3 H) 3.07 (s, 1 H) 3.55 (s, 3 H) 4.28 (m, 3 H) 7.09 (d, J=2.7 Hz, 1H) 7.34-7.40 (d, J=8.3 Hz, 2 H) 7.43 (d, J=2.8 Hz, 1 H) 7.65-7.71 (d, J=8.3 Hz, 2 H).

Step 6.2: ethyl 2-(N-(5-chloro-1-methyl-6-oxo-1,6-dihydropyridin-3-yl)-3-oxobutanamido)-2-(4-chlorophenyl)acetate

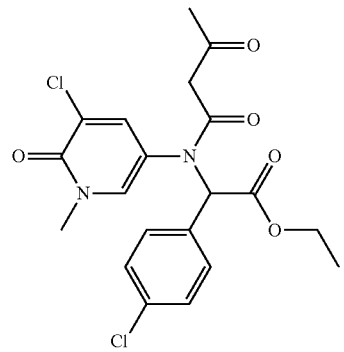 [SMILES: CCOC(=O)C(c1ccc(Cl)cc1)N(C(=O)CC(C)=O)c1cc(Cl)c(=O)n(C)c1]

The title compound was prepared in analogy to the procedure described in Example 1 using ethyl 2-((5-chloro-1-methyl-6-oxo-1,6-dihydropyridin-3-yl)amino)-2-(4-chlorophenyl)acetate (Step 1.1) and S-tert-butyl 3-oxobutanethioate (Step 1.5). $R_f$=0.46 (hexane/acetone 1:1); $t_R$: 0.94 min (LC-MS 1); ESI-MS: 439/441 [M+H]$^+$ (LC-MS 1).

Step 6.3: 3-acetyl-1-(5-chloro-1-methyl-6-oxo-1,6-dihydropyridin-3-yl)-5-(4-chlorophenyl)pyrrolidine-2,4-dione

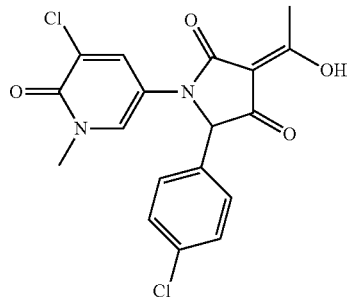 [SMILES: C/C(O)=C1/C(=O)C(c2ccc(Cl)cc2)N(c2cc(Cl)c(=O)n(C)c2)C1=O]

The title compound was prepared in analogy to the procedure described in Example 1 using ethyl 2-(N-(5-chloro-1-methyl-6-oxo-1,6-dihydropyridin-3-yl)-3-oxobutanamido)-2-(4-chlorophenyl)acetate (Step 6.2). $t_R$: 0.65 min (LC-MS 1); ESI-MS: 393/395 [M+H]$^+$ (LC-MS 1); $^1$H NMR (400 MHz, CDCl$_3$) δ ppm 2.44 (s, 3 H) 3.49 (s, 3 H) 4.96 (s, 1 H) 7.11 (d, J=8.4 Hz, 2 H) 7.31 (d, J=8.5 Hz, 2 H) 7.49 (d, J=2.7 Hz, 1 H) 7.54 (d, J=2.8 Hz, 1 H) 7.96 (s, 1 H).

EXAMPLE 7a 5-(5-chloro-1-methyl-6-oxo-1,6-dihydropyridin-3-yl)-6-(4-chlorophenyl)-1-(2-methoxypyridin-3-yl)-3-methyl-5,6-dihydropyrrolo[3,4-c]pyrazol-4(1H)-one and EXAMPLE 7b 5-(5-chloro-1-methyl-6-oxo-1,6-dihydropyridin-3-yl)-6-(4-chlorophenyl)-2-(2-methoxypyridin-3-yl)-3-methyl-5,6-dihydropyrrolo[3,4-c]pyrazol-4(2H)-one

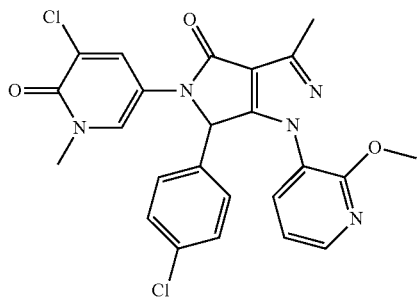

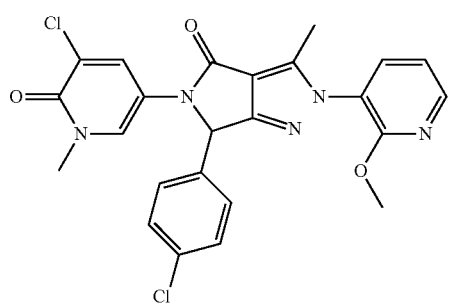

To a solution of 5-(5-chloro-1-methyl-6-oxo-1,6-dihydropyridin-3-yl)-6-(4-chlorophenyl)-3-methyl-5,6-dihydropyrrolo[3,4-c]pyrazol-4(2H)-one (Example 6) (100 mg, 0.257 mmol) (2-methoxypyrimidin-5-yl)boronic acid (79 mg, 0.514 mmol) and pyridine (0.042 mL, 0.514 mmol) in ACN (2 mL) was added under Ar Cu(OAc)$_2$ (93 mg, 0.514 mmol) and molecular sieve (50 mg). The reaction mixture was stirred at 65° C. and every 0.5 h 2 eq. of (2-methoxypyrimidin-5-yl)boronic acid and 1 eq. pyridine were added until the reaction was complete. The reaction mixture was added to ice-water and the product was extracted with CH$_2$Cl$_2$. Combined extracts were washed with H$_2$O, dried over MgSO$_4$, filtered and concentrated. The crude product was purified by silica gel column chromatography (hexane/EtOAc/MeOH 80:20:2 to 0:100:10) to afford a mixture of regioisomers which was separated by SFC (Silica (250×30 mm, 5 μm), gradient: 17-22% B in 9 min, A: scCO$_2$, B: MeOH; flow: 100 mL/min) to afford the title product 7a (28 mg, 22% yield) as a white solid. $t_R$: 0.979 min (UPLC 1); $t_R$: 0.97 min (LC-MS 1); ESI-MS: 496/498 [M+H]$^+$ (LC-MS 1); 1H NMR (400 MHz, DMSO-d$_6$) δ ppm 2.44 (s, 3 H) 3.45 (s, 3H) 3.96 (s, 3 H) 6.28 (s, 1 H) 7.00-7.07 (m, 3 H) 7.23 (d, J=8.4 Hz, 2 H) 7.77 (dd, J=7.7, 1.7 Hz, 1 H) 7.90-7.95 (m, 2 H) 8.15 (dd, J=5.0, 1.7 Hz, 1 H) and 7b (9 mg, 7% yield) as a light yellow solid. $t_R$: 0.980 min (UPLC 1); $t_R$: 0.96 min (LC-MS 1); ESI-MS: 496/498 [M+H]$^+$ (LC-MS 1); 1H NMR (400 MHz, DMSO-d$_6$) δ ppm 2.30 (s, 3 H) 3.47 (s, 3 H) 3.91 (s, 3 H) 6.35 (s, 1 H) 7.20 (dd, J=7.6, 5.0 Hz, 1 H) 7.35 (d, J=9.4 Hz, 2 H) 7.42 (d, J=9.4 Hz, 2 H) 7.90 (dd, J=7.6, 1.7 Hz, 1 H) 7.97-8.02 (m, 2 H) 8.00 (s, 2 H) 8.37 (dd, J=5.0, 1.7 Hz, 1 H).

EXAMPLE 8a 5-(5-chloro-1-methyl-6-oxo-1,6-dihydropyridin-3-yl)-6-(4-chlorophenyl)-1-(2-methoxypyrimidin-5-yl)-3-methyl-5,6-dihydropyrrolo[3,4-c]pyrazol-4(1H)-one and EXAMPLE 8b 5-(5-chloro-1-methyl-6-oxo-1,6-dihydropyridin-3-yl)-6-(4-chlorophenyl)-2-(2-methoxypyrimidin-5-yl)-3-methyl-5,6-dihydropyrrolo[3,4-c]pyrazol-4(2H)-one

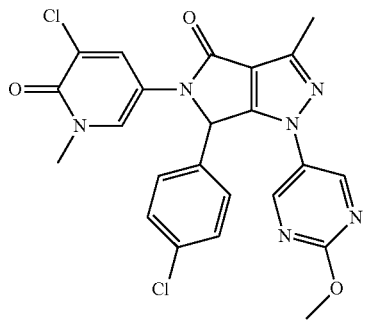

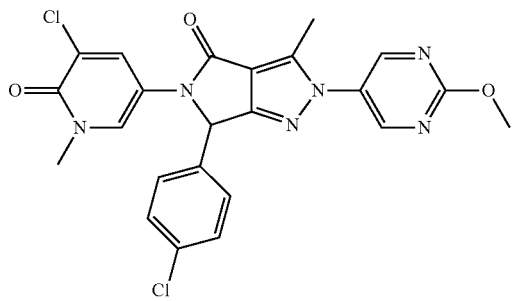

The title compounds were prepared in analogy to the procedure described in Example 7a and 7b using 5-(5-chloro-1-methyl-6-oxo-1,6-dihydropyridin-3-yl)-6-(4-chlorophenyl)-3-methyl-5,6-dihydropyrrolo[3,4-c]pyrazol-4(2H)-one (Example 6) and (2-methoxypyrimidin-5-yl) boronic acid. The mixture of regioisomers was separated by SFC (Silica (250×30 mm, 5 μm), gradient: 21-26% B in 11 min, A: scCO$_2$, B: MeOH; flow: 100 mL/min) to provide the title product 8a (19 mg, 15% yield) as a white solid. $t_R$: 0.916 min (UPLC 1); $t_R$: 0.91 min (LC-MS 1); ESI-MS: 497/499 [M+H]$^+$ (LC-MS 1); 1H NMR (400 MHz, DMSO-d$_6$) δ ppm 2.46 (s, 3 H) 3.46 (s, 3 H) 3.93 (s, 3 H) 6.78 (s, 1 H) 7.28 (d, J=8.3 Hz, 2 H) 7.36 (d, J=8.3 Hz, 2 H) 7.85 (s, 2 H) 8.75 (s, 2 H) and 7b (41 mg, 32% yield) as a white solid. $t_R$: 0.897 min (UPLC 1); $t_R$: 0.89 min (LC-MS 1); ESI-MS: 497/499 [M+H]$^+$ (LC-MS 1); 1H NMR (400 MHz, DMSO-d$_6$) δ ppm 2.53 (s, 3 H) 3.47 (s, 3 H) 4.00 (s, 3 H) 6.37 (s, 1 H) 7.36 (d, J=8.8 Hz, 2 H) 7.43 (d, J=8.8 Hz, 2 H) 7.99-8.01 (m, 2 H) 8.88 (s, 2 H).

EXAMPLE 9

6-(4-chlorophenyl)-5-(1,5-dimethyl-6-oxo-1,6-dihydropyridin-3-yl)-3-methyl-5,6-dihydropyrrolo[3,4-c]pyrazol-4(2H)-one

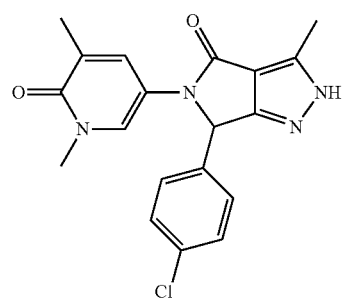 [SMILES: Cc1[nH]nc2c1C(=O)N(c1cc(C)c(=O)n(C)c1)C2c1ccc(Cl)cc1]

The title compound was prepared in analogy to the procedure described in Example 1 using 3-acetyl-5-(4-chlorophenyl)-1-(1,5-dimethyl-6-oxo-1,6-dihydropyridin-3-yl) pyrrolidine-2,4-dione (Step 9.2) and hydrazine hydrate. R$_f$=0.33 (CH$_2$Cl$_2$/MeOH 19:1); $t_R$: 0.69 min (LC-MS 1); ESI-MS: 369/371 [M+H]$^+$ (LC-MS 1); $^1$H NMR (400 MHz, DMSO-d$_6$) δ ppm 1.91-1.96 (m, 3 H) 2.42 (s, 3 H) 3.31 (s., 1 H) 6.15 (s, 1 H) 7.25 (d, J=8.4 Hz, 2 H) 7.38 (d, J=8.4 Hz, 2 H) 7.43 (br. s., 1 H) 7.71 (d, J=2.4 Hz, 1 H) 13.19 (s, 1 H).

Step 9.1 ethyl 2-(4-chlorophenyl)-2-(N-(1,5-dimethyl-6-oxo-1,6-dihydropyridin-3-yl)-3-oxobutanamido)acetate

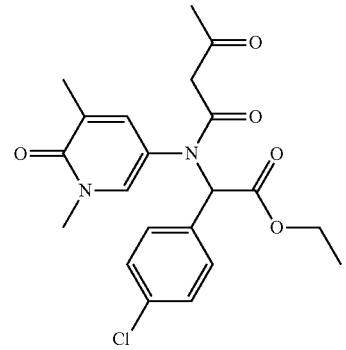 [SMILES: CCOC(=O)C(c1ccc(Cl)cc1)N(C(=O)CC(C)=O)c1cc(C)c(=O)n(C)c1]

The title compound was prepared in analogy to the procedure described in Example 1 using ethyl 2-(4-chlorophenyl)-2-((1,5-dimethyl-6-oxo-1,6-dihydropyridin-3-yl) amino)acetate (Step 1.1) and S-tert-butyl 3-oxobutanethioate. R$_f$=0.33 (hexane/acetone 1:1); $t_R$: 0.89 min (LC-MS 1); ESI-MS: 417/419 [M+H]$^+$ (LC-MS 1).

Step 9.2: ethyl 2-(4-chlorophenyl)-2-(N-(1,5-dimethyl-6-oxo-1,6-dihydropyridin-3-yl)-3-oxobutanamido)acetate

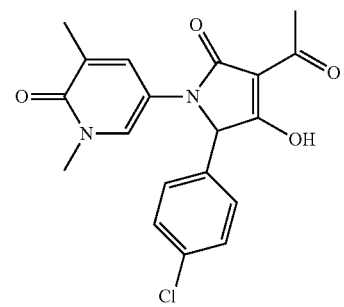 [SMILES: CC(=O)C1=C(O)C(c2ccc(Cl)cc2)N(c2cc(C)c(=O)n(C)c2)C1=O]

The title compound was prepared in analogy to the procedure described in Example 1 using ethyl 2-(4-chlorophenyl)-2-(N-(1,5-dimethyl-6-oxo-1,6-dihydropyridin-3-yl)-3-oxobutanamido)-acetate (Step 9.1). $t_R$: 0.65 min (LC-MS 1); ESI-MS: 373/375 [M+H]$^+$ (LC-MS 1); $^1$H NMR (400 MHz, CDCl$_3$) δ ppm 2.02 (s, 3 H) 2.40-2.45 (m, 3 H) 3.43 (s, 3 H) 4.98 (s, 1 H) 7.12 (d, J=9.0 Hz, 2 H) 7.29 (d, J=9.0 Hz, 2 H) 7.40-7.44 (m, 2 H) 7.95 (s, 1 H).

EXAMPLE 10

6-(4-chlorophenyl)-5-(1,5-dimethyl-6-oxo-1,6-dihydropyridin-3-yl)-1,3-dimethyl-5,6-dihydropyrrolo[3,4-c]pyrazol-4(1H)-one

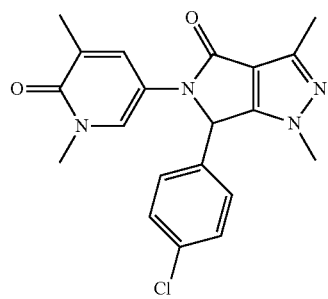 [SMILES: Cc1nn(C)c2c1C(=O)N(c1cc(C)c(=O)n(C)c1)C2c1ccc(Cl)cc1]

The title compound was prepared in analogy to the procedure described in Example 1, using 3-acetyl-5-(4-chlorophenyl)-1-(1,5-dimethyl-6-oxo-1,6-dihydropyridin-3-yl)pyrrolidine-2,4-dione (Step 9.2) and methylhydrazine. $R_f$=0.33 (EtOAc/MeOH 4:1); $t_R$: 0.77 min (LC-MS 1); ESI-MS: 383/385 [M+H]$^+$ (LC-MS 1); $^1$H NMR (400 MHz, DMSO-d$_6$) δ ppm 1.93 (s, 3 H) 2.30 (s, 3 H) 3.36 (s, 3H) 3.46 (s, 3 H) 6.25 (s, 1 H) 7.25-7.36 (m, 3 H) 7.44 (d, J=8.4 Hz, 2 H) 7.64 (d, J=2.7 Hz, 1 H).

EXAMPLE 11

6-(4-chlorophenyl)-1-cyclopropyl-5-(1,5-dimethyl-6-oxo-1,6-dihydropyridin-3-yl)-3-methyl-5,6-dihydropyrrolo[3,4-c]pyrazol-4(1H)-one

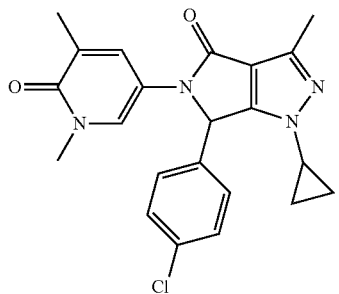 [SMILES: Cc1nn(C2CC2)c2c1C(=O)N(c1cc(C)c(=O)n(C)c1)C2c1ccc(Cl)cc1]

The title compound was prepared in analogy to the procedure described in Example 13, using 3-acetyl-5-(4-chlorophenyl)-1-(1,5-dimethyl-6-oxo-1,6-dihydropyridin-3-yl)pyrrolidine-2,4-dione (Step 9.2) and cyclopropylhydrazine hydrochloride. $R_f$=0.26 (EtOAc/MeOH 9:1); $t_R$: 0.86 min (LC-MS 1); ESI-MS: 409/411 [M+H]$^+$ (LC-MS 1); $^1$H NMR (600 MHz, DMSO-d$_6$) δ ppm 0.57-0.83 (m, 3 H) 1.10 (m, 1 H) 1.92 (s, 3 H) 2.28 (s, 3 H) 3.11 (m, 1 H) 3.35 (s, 3 H) 6.31 (s, 1 H) 7.32 (d, J=8.0 Hz, 2 H) 7.37 (br. s., 1 H) 7.41 (d, J=8.0 Hz, 2 H) 7.64 (br. s., 1 H).

EXAMPLE 12

6-(4-chlorophenyl)-5-(1,5-dimethyl-6-oxo-1,6-dihydropyridin-3-yl)-1-isopropyl-3-methyl-5,6-dihydropyrrolo[3,4-c]pyrazol-4(1H)-one

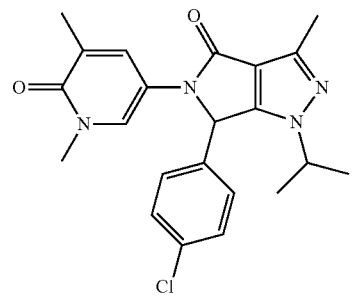 [SMILES: Cc1nn(C(C)C)c2c1C(=O)N(c1cc(C)c(=O)n(C)c1)C2c1ccc(Cl)cc1]

The title compound was prepared in analogy to the procedure described in Example 1, using 3-acetyl-5-(4-chlorophenyl)-1-(1,5-dimethyl-6-oxo-1,6-dihydropyridin-3-yl)pyrrolidine-2,4-dione (Step 9.2) and isopropylhydrazine. $R_f$=0.35 (EtOAc/MeOH 9:1); $t_R$: 0.91 min (LC-MS 1); ESI-MS: 411/413 [M+H]$^+$ (LC-MS 1); $^1$H NMR (400 MHz, DMSO-d$_6$) δ ppm 1.01 (d, J=6.7 Hz, 4 H) 1.21 (d, J=6.6 Hz, 4 H) 1.93 (s, 3 H) 2.32 (s, 3 H) 3.36 (s, 3 H) 4.03-4.14 (m, 1 H) 6.30 (s, 1 H) 7.31 (d, J=8.5 Hz, 2 H) 7.35 (d, J=1.6 Hz, 1 H) 7.44 (d, J=8.4 Hz, 2 H) 7.64 (d, J=2.69 Hz, 1 H).

EXAMPLE 13

6-(4-chlorophenyl)-5-(1,5-dimethyl-6-oxo-1,6-dihydropyridin-3-yl)-1-(4-methoxyphenyl)-3-methyl-5,6-dihydropyrrolo[3,4-c]pyrazol-4(1H)-one

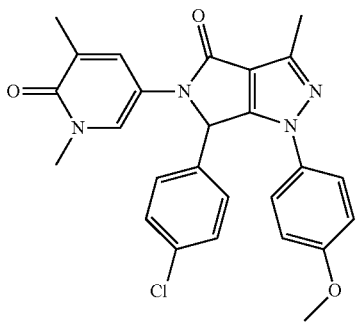 [SMILES: COc1ccc(-n2nc(C)c3c2C(c2ccc(Cl)cc2)N(c2cc(C)c(=O)n(C)c2)C3=O)cc1]

To a solution of (4-methoxyphenyl)hydrazine hydrochloride (141 mg, 0.805 mmol) and NEt$_3$ (0.110 mL, 0.789 mmol) in EtOH (8 mL) was added 3-acetyl-5-(4-chlorophenyl)-1-(1,5-dimethyl-6-oxo-1,6-dihydropyridin-3-yl)pyrrolidine-2,4-dione (Step 9.2) (300 mg, 0.805 mmol) and the reaction mixture was stirred for 4 h at RT. To the reaction mixture was added AcOH (4 mL) and sulfamic acid (117 mg, 1.21 mmol) and the mixture was heated in the MW for 2 h at 100° C. and 2 h at 120° C. The reaction mixture was concentrated and the residue was dissolved in sat. NaHCO$_3$ and extracted with EtOAc. Combined extracts were washed with brine, dried over MgSO$_4$, filtered and concentrated. The crude product was purified by silica gel column chromatography (hexane/EtOAc/MeOH 50:50:5 to 0:100:10) to afford the title product (288 mg, 75% yield) as a yellow foam. $R_f$=0.45 (EtOAc/MeOH 9:1); $t_R$: 1.015 min (UPLC 1); $t_R$: 0.99 min (LC-MS 1); ESI-MS: 475/477 [M+H]$^+$ (LC-MS 1); $^1$H NMR (400 MHz, DMSO-$d_6$) δ ppm 1.95 (s, 3 H) 2.43 (s, 3 H) 3.37 (s, 3 H) 3.75 (s, 3 H) 6.71 (s, 1 H) 6.93 (d, J=8.5 Hz, 2 H) 7.21 (d, J=8.6 Hz, 2 H) 7.30 (d, J=8.2 Hz, 2 H) 7.37 (d, J=1.5 Hz, 1 H) 7.45 (d, J=7.9 Hz, 2 H) 7.63 (d, J=2.6 Hz, 1 H).

EXAMPLE 14

6-(4-chlorophenyl)-2-(2,4-dimethoxypyrimidin-5-yl)-5-(1,5-dimethyl-6-oxo-1,6-dihydropyridin-3-yl)-3-methyl-5,6-dihydropyrrolo[3,4-c]pyrazol-4(2H)-one

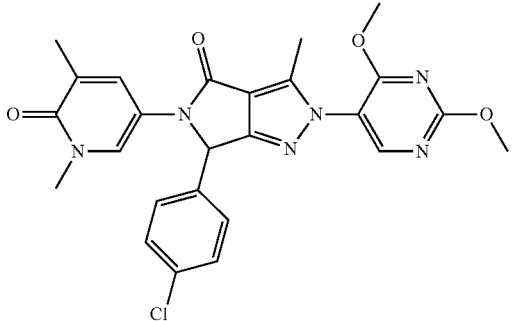 [SMILES: COc1ncc(-n2nc3c(c2C)C(=O)N(c2cc(C)c(=O)n(C)c2)C3c2ccc(Cl)cc2)c(OC)n1]

The title compound was prepared in analogy to the procedure described in Example 13, using 3-acetyl-5-(4-chlorophenyl)-1-(1,5-dimethyl-6-oxo-1,6-dihydropyridin-3-yl)pyrrolidine-2,4-dione (Step 9.2) and 5-hydrazinyl-2,4-dimethoxypyrimidine (Step 14.2). $R_f$=0.61 (CH$_2$Cl$_2$/MeOH 9:1); $t_R$: 0.88 min (LC-MS 1); ESI-MS: 507/509 [M+H]$^+$ (LC-MS 1); $^1$H NMR (400 MHz, DMSO-$d_6$) δ ppm 1.93 (s, 3 H) 2.41 (s, 3 H) 3.36 (s, 3 H) 3.84 (s, 3 H) 3.91 (s, 3 H) 6.23 (s, 1 H) 7.06 (d, J=8.4 Hz, 2 H) 7.30 (d, J=8.4 Hz, 2 H) 7.37-7.42 (m, 1 H) 7.66-7.73 (m, 1 H) 8.35 (s, 1 H).

Step 14.1: di-tert-butyl 1-(2,4-dimethoxypyrimidin-5-yl)hydrazine-1,2-dicarboxylate

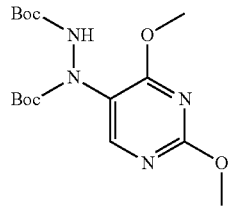 [SMILES: COc1ncc(N(NC(=O)OC(C)(C)C)C(=O)OC(C)(C)C)c(OC)n1]

To a stirred solution of 5-bromo-2,4-dimethoxypyrimidine (400 g, 1.826 mol) in anhydrous THF (3 L) under Ar and cooled down to 0° C. was added dropwise TurboGrignard (1.821 L, 2.37 mol). The resulting mixture was stirred at 0° C. until exothermic ceased then, allowed to warm up and stir at RT for 30 min. A solution of di-tert-butyl azodicarboxylate in anhydrous THF (1 L) was added dropwise to the mixture and the reaction was stirred at RT for 1 h. The reaction was slowly quenched with a sat. aq. NH$_4$Cl solution, diluted with EtOAc and water. The aq. phase was extracted with EtOAc, combined organic extracts were washed with brine, dried over Na$_2$SO$_4$, filtered and concentrated. The resulting yellow oil was dissolved in hexane and the suspension was stirred at 0° C. for 3 h. The precipitate was filtrated off and dried to afford a first batch of white crystals. The mother liquor was concentrated and purified by silica gel column chromatography to afford a second batch of white crystals. The two batches were combined to afford the title product (507 g, 1.369 mol, 75% yield) as white crystals. $t_R$: 1.03 min (LC-MS 1); ESI-MS: 371 [M+H]$^+$, ESI-MS: 369 [M−H]$^−$ (LC-MS 1).

Step 14.2: 5-hydrazinyl-2,4-dimethoxypyrimidine

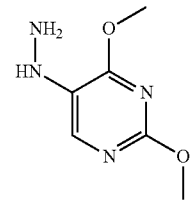

To a solution of di-tert-butyl 1-(2,4-dimethoxypyrimidin-5-yl)hydrazine-1,2-dicarboxylate (Step 14.1) (453 g, 1.223 mol) in MeOH (2.5 L) was added at 0° C. 4N HCl in dioxane (2.5 L, 10 mol) and the resulting mixture was stirred at RT overnight. The reaction mixture was concentrated and residue was taken up in 4N NH$_3$ (2 L), stirred for 1 h, and evaporated again. The dried residue was suspended in CH$_2$Cl$_2$ (2 L), the salts filtered off and the filtrate was concentrated. The crude product was stirred with Et$_2$O (2 L) at 0° C. for 30 min. The resulting suspension was filtrated again and the filtrate was concentrated to afford the title product (150 g, 864 mmol, 70% yield) as light beige solid. $t_R$: 0.32 min (LC-MS 1); ESI-MS: 171.1 [M+H]$^+$ (LC-MS 1).

EXAMPLE 15

6-(4-chlorophenyl)-5-(1,5-dimethyl-6-oxo-1,6-dihydropyridin-3-yl)-3-(2-methoxypyridin-3-yl)-1-methyl-5,6-dihydropyrrolo[3,4-c]pyrazol-4(1H)-one

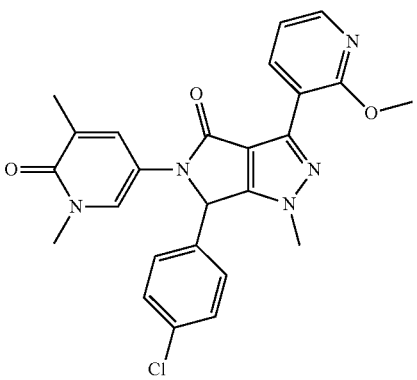 [SMILES: COc1ncccc1-c1nn(C)c2c1C(=O)N(c1cc(C)c(=O)n(C)c1)C2c1ccc(Cl)cc1]

The title compound was prepared in analogy to the procedure described in Example 1, using 5-(4-chlorophenyl)-1-(1,5-dimethyl-6-oxo-1,6-dihydropyridin-3-yl)-3-(2- methoxynicotinoyl)pyrrolidine-2,4-dione (Step 15.4) and methylhydrazine. $t_R$: 0.89 min (LC-MS 1); ESI-MS: 476/478 [M+H]$^+$ (LC-MS 1); $^1$H NMR (400 MHz, DMSO-d$_6$) δ ppm 1.94 (s, 3 H) 3.37 (s, 3 H) 3.59 (s, 3 H) 3.92 (s, 3 H) 6.36 (s, 1 H) 7.12 (dd, J=7.4, 4.9 Hz, 1 H) 7.33-7.41 (m, 3 H) 7.47 (d, J=8.7 Hz, 2 H) 7.69 (d, J=2.7 Hz, 1 H) 8.24 (dd, J=4.9, 1.8 Hz, 1 H) 8.32 (dd, J=7.4, 1.9 Hz, 1 H).

Step 15.1: S-pyridin-2-yl 2-methoxypyridine-3-carbothioate

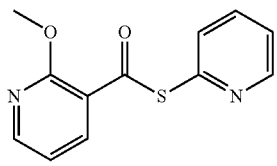 [SMILES: COc1ncccc1C(=O)Sc1ccccn1]

To a solution of 2-methoxynicotinic acid (4.59 g, 30 mmol) and 1,2-di(pyridin-2-yl)disulfane (6.74 g, 30 mmol) in THF (60 mL) was added under Ar triphenylphosphine and the reaction mixture was stirred for 6 h at RT. The reaction mixture was concentrated and the residual oil was purified by silica gel column chromatography (hexane/EtOAc 80:20 to 50:50) to afford the title product (6.6 g, 74% yield) as a white solid. R$_f$=0.36 (hexane/EtOAc 1:1); $t_R$: 0.803 min (UPLC 1); $t_R$: 0.87 min (LC-MS 1); ESI-MS: 247 [M+H]$^+$ (LC-MS 1); $^1$H NMR (400 MHz, CDCl$_3$) δ ppm 4.05 (s, 3 H) 6.95 (dd, J=7.58, 4.89 Hz, 1 H) 7.26 (ddd, J=7.3, 4.9, 1.1 Hz, 1 H) 7.66 (d, J=8.6 Hz, 1 H) 7.7 (td, J=7.8, 1.8 Hz, 1 H) 8.12 (dd, J=7.6, 2.0 Hz, 1 H) 8.29 (dd, J=4.9, 1.8 Hz, 1 H) 8.58-8.64 (m, 1 H).

Step 15.2: S-tert-butyl 3-(2-methoxypyridin-3-yl)-3-oxopropanethioate

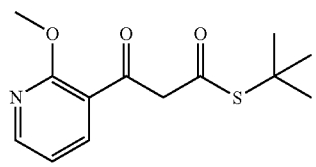 [SMILES: COc1ncccc1C(=O)CC(=O)SC(C)(C)C]

To a solution of S-pyridin-2-yl 2-methoxypyridine-3-carbothioate (1.11 g, 4.5 mmol) in THF (30 mL) was added under Ar a 1M solution of LiHMDS in THF (13.5 mL, 15.5 mmol) below −70° C. To this solution was added a solution of S-tert-butyl ethanethioate in THF (3 mL) at −78° C. After stirring for 15 min at −78° C. the reaction mixture was poured onto 1N aq. HCl and the product was extracted with EtOAc. Combined extracts were washed with sat. NaHCO$_3$ solution and brine, dried over MgSO$_4$, filtered and concentrated. The crude product was purified by silica gel column chromatography (hexane/EtOAc/MeOH 50:50:5 to 0:100:10) to afford the title product (288 mg, 75% yield) as a colorless oil. R$_f$=0.45 (EtOAc/MeOH 9:1); $t_R$: 1.221 min (UPLC 1); $t_R$: 1.14 min (LC-MS 1); ESI-MS: 268 [M+H]$^+$ (LC-MS 1); $^1$H NMR (400 MHz, CDCl$_3$) δ ppm 1.41 (s, 3.5 H) 1.47-1.51 (m, 5.5 H) 3.38 and 3.98 (s, 3 H) 4.10 (s, 1.2 H) 6.43-6.49 (m, 0.4 H) 6.87-6.97 (m, 1 H) 8.09-8.29 (m, 2 H) 13.38 (s, 0.4 H).

Step 15.3: ethyl 2-(4-chlorophenyl)-2-(N-(1,5-dimethyl-6-oxo-1,6-dihydropyridin-3-yl)-3-(2-methoxypyridin-3-yl)-3-oxopropanamido)acetate

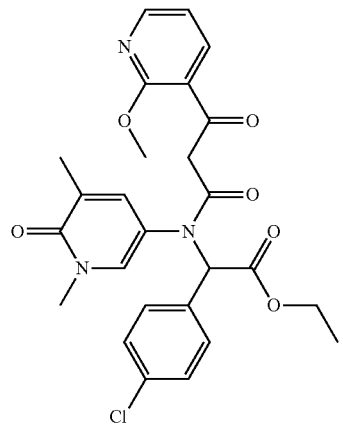 [SMILES: CCOC(=O)C(c1ccc(Cl)cc1)N(C(=O)CC(=O)c1cccnc1OC)c1cc(C)c(=O)n(C)c1]

The title compound was prepared in analogy to the procedure described in Example 1 using S-tert-butyl 3-(2-methoxypyridin-3-yl)-3-oxopropanethioate (Step 15.2) and 2-(4-chlorophenyl)-2-((1,5-dimethyl-6-oxo-1,6-dihydropyridin-3-yl)amino)acetate (Step 1.1). R$_f$=0.42 (EtOAc); $t_R$: 1.00 min and 1.22 min (LC-MS 1); ESI-MS: 512/514 [M+H]$^+$ (LC-MS 1).

Step 15.4: 5-(4-chlorophenyl)-1-(1,5-dimethyl-6-oxo-1,6-dihydropyridin-3-yl)-3-(2-methoxynicotinoyl)pyrrolidine-2,4-dione

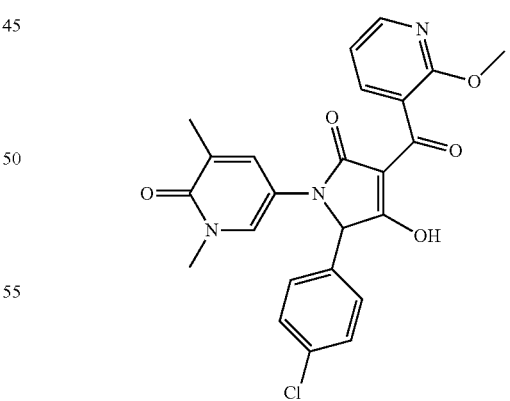

The title compound was prepared in analogy to the procedure described in Example 1, Step 13, using ethyl 2-(4-chlorophenyl)-2-(N-(1,5-dimethyl-6-oxo-1,6-dihydropyridin-3-yl)-3-(2-methoxypyridin-3-yl)-3-oxopropanamido)acetate (Step 15.3). $t_R$: 0.60 min (LC-MS 1); ESI-MS: 466/468 [M+H]$^+$ (LC-MS 1).

EXAMPLE 16

(R)-6-(4-chlorophenyl)-5-(1,5-dimethyl-6-oxo-1,6-dihydropyridin-3-yl)-3-(2-methoxypyridin-3-yl)-1-methyl-5,6-dihydropyrrolo[3,4-c]pyrazol-4(1H)-one

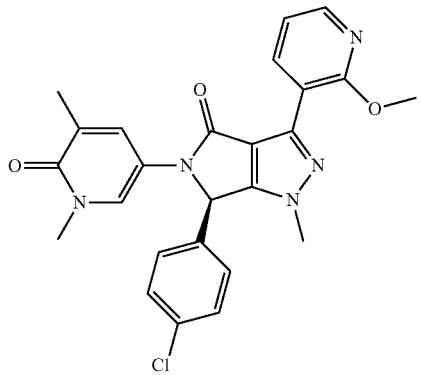 [SMILES: COc1ncccc1-c1nn(C)c2c1C(=O)N(c1cc(C)c(=O)n(C)c1)[C@@H]2c1ccc(Cl)cc1]

The title compound (159 mg, 35% yield) was obtained enantiomerically pure (98% ee) as a white solid after chiral preparative chromatography (system: SFC-PicLab-Prep 100; column: Chiralpak AD-H 50×250 mm; mobile phase: scCO₂/MeOH 40:60 (isocratic); flow: 80 g/min; detection UV: 245 nm) of the racemic mixture of 6-(4-chlorophenyl)-5-(1,5-dimethyl-6-oxo-1,6-dihydropyridin-3-yl)-3-(2-methoxypyridin-3-yl)-1-methyl-5,6-dihydropyrrolo[3,4-c]pyrazol-4(1H)-one (Example 15) (450 mg, 0.927 mmol) and trituration of the resulting residue in Et₂O. $t_R$: 0.89 min (LC-MS 1); ESI-MS: 476/478 [M+H]⁺ (LC-MS 1); ¹H NMR (400 MHz, DMSO-d₆) δ ppm 1.94 (s, 3 H) 3.37 (s, 3 H) 3.59 (s, 3 H) 3.92 (s, 3 H) 6.36 (s, 1 H) 7.12 (dd, J=7.4, 4.9 Hz, 1 H) 7.33-7.41 (m, 3 H) 7.47 (d, J=8.7 Hz, 2 H) 7.69 (d, J=2.7 Hz, 1 H) 8.24 (dd, J=4.9, 1.8 Hz, 1 H) 8.32 (dd, J=7.4, 1.9 Hz, 1 H. The second enantiomer, (S)-6-(4-chlorophenyl)-5-(1,5-dimethyl-6-oxo-1,6-dihydropyridin-3-yl)-3-(2-methoxypyridin-3-yl)-1-methyl-5,6-dihydropyrrolo[3,4-c]pyrazol-4(1H)-one, was obtained via the same separation enantiomerically pure (98% ee) as a white solid (177 mg, 39% yield).

EXAMPLE 17a 6-(4-chlorophenyl)-5-(1,5-dimethyl-6-oxo-1,6-dihydropyridin-3-yl)-1-(2-methoxypyridin-3-yl)-3-methyl-5,6-dihydropyrrolo[3,4-c]pyrazol-4(1H)-one and

EXAMPLE 17b 6-(4-chlorophenyl)-5-(1,5-dimethyl-6-oxo-1,6-dihydropyridin-3-yl)-2-(2-methoxypyridin-3-yl)-3-methyl-5,6-dihydropyrrolo[3,4-c]pyrazol-4(2H)-one

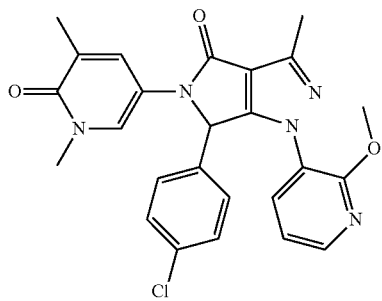

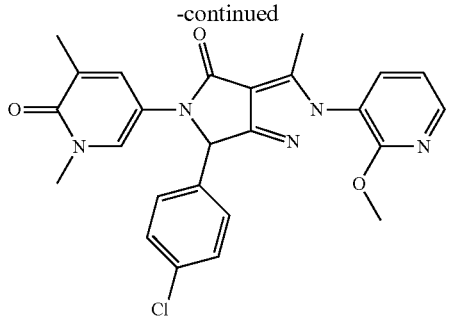

The title compounds 17a and 17b were prepared in analogy to the procedure described in Example 7a using 5-(5-chloro-1-methyl-6-oxo-1,6-dihydropyridin-3-yl)-6-(4-chlorophenyl)-3-methyl-5,6-dihydropyrrolo[3,4-c]pyrazol-4(2H)-one (Example 6) and (2-methoxypyridin-3-yl)-boronic acid. The mixture of regioisomers was separated by SFC (Silica (250×30 mm, 5 μm), isocratic 7% B in 60 min, A: scCO₂, B: MeOH; flow: 100 mL/min) to provide the title product 17a as a white solid. $R_f$=0.44 (EtOAc/MeOH 9:1); $t_R$: 0.927 min (UPLC 1); $t_R$: 0.93 min (LC-MS 1); ESI-MS: 476/478 [M+H]⁺ (LC-MS 1); ¹H NMR (400 MHz, DMSO-d₆) δ ppm 1.93 (s, 3 H) 2.43 (s, 3 H) 3.37 (s, 3 H) 3.96 (s, 3 H) 6.22 (s, 1 H) 6.98-7.06 (m, 3 H) 7.23 (d, J=8.1 Hz, 2 H) 7.36-7.40 (m, 1 H) 7.71 (d, J=2.7 Hz, 1 H) 7.77 (dd, J=7.7, 1.7 Hz, 1 H) 8.14 (dd, J=4.9, 1.7 Hz, 1 H and 17b as a white solid. $R_f$=0.44 (EtOAc/MeOH 9:1); $t_R$: 0.927 min (UPLC 1); $t_R$: 0.93 min (LC-MS 1); ESI-MS: 476/478 [M+H]⁺ (LC-MS 1); ¹H NMR (400 MHz, DMSO-d₆) δ ppm 1.96 (s, 3 H) 2.30 (s, 3 H) 3.39 (s, 3 H) 3.91 (s, 3 H) 6.30 (s, 1 H) 7.20 (dd, J=7.6, 5.0 Hz, 1 H) 7.32 (d, J=8.8 Hz, 2 H) 7.41 (d, J=9.1 Hz, 2 H) 7.48 (m, 1 H) 7.77 (d, J=2.7 Hz, 1 H) 7.89 (dd, J=7.6, 1.7 Hz, 1 H) 8.37 (dd, J=4.9, 1.8 Hz, 1 H).

EXAMPLE 18a 6-(4-chlorophenyl)-5-(1,5-dimethyl-6-oxo-1,6-dihydropyridin-3-yl)-1-(2-ethoxypyridin-3-yl)-3-methyl-5,6-dihydropyrrolo[3,4-c]pyrazol-4(1H)-one and

EXAMPLE 18b 6-(4-chlorophenyl)-5-(1,5-dimethyl-6-oxo-1,6-dihydropyridin-3-yl)-2-(2-ethoxypyridin-3-yl)-3-methyl-5,6-dihydropyrrolo[3,4-c]pyrazol-4(2H)-one

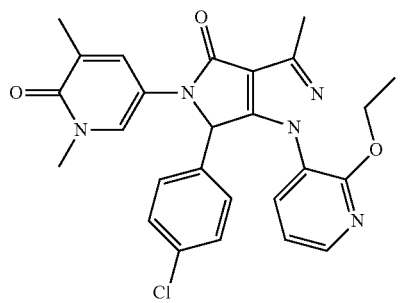

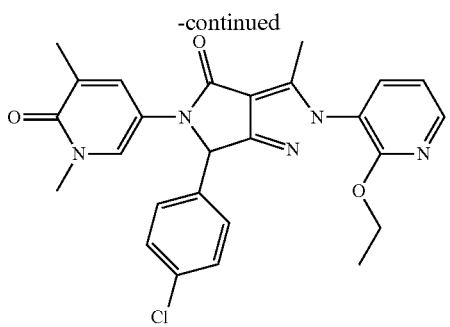

The title compounds 18a and 18b were prepared in analogy to the procedure described in Example 7 using 5-(5-chloro-1-methyl-6-oxo-1,6-dihydropyridin-3-yl)-6-(4-chlorophenyl)-3-methyl-5,6-dihydropyrrolo[3,4-c]pyrazol-4(2H)-one (Example 6) and (2-ethoxypyridin-3-yl)-boronic acid. The mixture of regioisomers was separated by SFC (Silica (250×30 mm, 5 μm), gradient 18-23% B in 11 min, A: scCO$_2$, B: MeOH; flow: 100 mL/min) to provide the title product 18a as a white solid. $R_f$=0.49 (EtOAc/MeOH 9:1); $t_R$: 0.992 min (UPLC 1); $t_R$: 0.99 min (LC-MS 1); ESI-MS: 490/492 [M+H]$^+$ (LC-MS 1); $^1$H NMR (400 MHz, DMSO-d$_6$) δ ppm 1.32 (t, J=8.1 Hz, 3 H) 1.92 (s, 3 H) 2.42 (s, 3 H) 3.36 (s, 3 H) 4.36 (m, 1H) 4.43 (m, 1 H) 6.13 (s, 1 H) 6.96-7.06 (m, 3 H) 7.20 (d, J=8.1 Hz, 2 H) 7.33 (m, 1 H) 7.66 (d, J=2.7 Hz, 1 H) 7.71 (dd, J=7.7, 1.7 Hz, 1 H) 8.13 (m, 1 H) and 18b as a white solid. $R_f$=0.46 (EtOAc/MeOH 9:1); $t_R$: 1.006 min (UPLC 1); $t_R$: 0.99 min (LC-MS 1); ESI-MS: 490/492 [M+H]$^+$ (LC-MS 1); $^1$H NMR (400 MHz, DMSO-d$_6$) δ ppm 1.24 (t, J=8.1 Hz, 3 H) 1.95 (s, 3 H) 2.31 (s, 3 H) 3.38 (s, 3 H) 4.37 (q, J=8.1 Hz, 2 H) 6.29 (s, 1 H) 7.16 (m, 1 H) 7.32 (d, J=8.1 Hz, 2 H) 7.39 (d, J=8.1 Hz, 2 H) 7.47 (m, 1 H) 7.76 (m, 1 H) 7.85 (m, 1 H) 8.33 (m, 1 H).

EXAMPLE 19

6-(4-chlorophenyl)-5-(1,5-dimethyl-6-oxo-1,6-dihydropyridin-3-yl)-1-(2-fluoropyridin-3-yl)-3-methyl-5,6-dihydropyrrolo[3,4-c]pyrazol-4(1H)-one

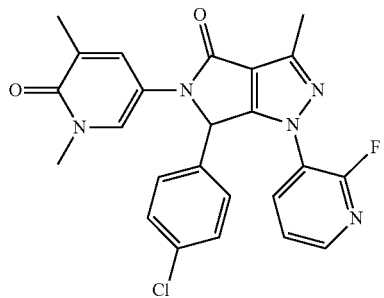 [SMILES: Cc1nn(-c2cccnc2F)c2c1C(=O)N(c1cc(C)c(=O)n(C)c1)C2c1ccc(Cl)cc1]

The title compound was prepared in analogy to the procedure described in Example 7 using 5-(5-chloro-1-methyl-6-oxo-1,6-dihydropyridin-3-yl)-6-(4-chlorophenyl)-3-methyl-5,6-dihydropyrrolo[3,4-c]pyrazol-4(2H)-one (Example 6) and (2-fluoropyridin-3-yl)boronic acid. $R_f$=0.54 (EtOAc/MeOH 19:1); $t_R$: 0.886 min (UPLC 1); $t_R$: 0.89 min (LC-MS 1); ESI-MS: 464/466 [M+H]$^+$ (LC-MS 1); $^1$H NMR (400 MHz, DMSO-d$_6$) δ ppm 1.93 (s, 3 H) 2.45 (s, 3 H) 3.35 (s, 3 H) 6.44 (s, 1 H) 7.13 (d, J=8.1 Hz, 2 H) 7.24 (d, J=8.1 Hz, 2 H) 7.41 (m, 1 H) 7.46 (dd, J=7.7, 1.7 Hz, 1 H) 7.73 (m, 1 H) 8.09 (m, 1 H) 8.21 (m, 1 H).

EXAMPLE 20a 6-(4-chlorophenyl)-5-(1,5-dimethyl-6-oxo-1,6-dihydropyridin-3-yl)-2-(6-methoxypyridin-3-yl)-3-methyl-5,6-dihydropyrrolo[3,4-c]pyrazol-4(2H)-one
and EXAMPLE 20b 6-(4-chlorophenyl)-5-(1,5-dimethyl-6-oxo-1,6-dihydropyridin-3-yl)-1-(6-methoxypyridin-3-yl)-3-methyl-5,6-dihydropyrrolo[3,4-c]pyrazol-4(1H)-one The title compounds 20a and 20b were prepared in analogy to the procedure described in Example 7 using 5-(5-chloro-1-methyl-6-oxo-1,6-dihydropyridin-3-yl)-6-(4-chlorophenyl)-3-methyl-5,6-dihydropyrrolo[3,4-c]pyrazol-4(2H)-one (Example 6) and (6-methoxypyridin-3-yl)boronic acid. The mixture of regioisomers was separated by SFC (DEAP (250×30 mm, 5 μm), gradient 7-12% B in 11 min, A: scCO$_2$, B: MeOH; flow: 100 mL/min) to provide the title product 20a as a white solid. $t_R$: 0.957 min (UPLC 1); $t_R$: 0.95 min (LC-MS 1); ESI-MS: 476/478 [M+H]$^+$ (LC-MS 1); $^1$H NMR (400 MHz, DMSO-d$_6$) δ ppm 1.96 (s, 3 H) 2.48 (s, 3 H) 3.39 (s, 3 H) 3.92 (s, 3 H) 6.31 (s, 1 H) 7.00 (d, J=8.8 Hz, 1 H) 7.33 (d, J=8.9 Hz, 2 H) 7.41 (d, J=9.1 Hz, 2 H) 7.47 (d, J=1.6 Hz, 1 H) 7.77 (d, J=2.7 Hz, 1 H) 7.92 (dd, J=8.9, 2.7 Hz, 1 H) 8.40 (d, J=2.7 Hz, 1 H) and 20b as a white solid. $t_R$: 0.967 min (UPLC 1); $t_R$: 0.96 min (LC-MS 1); ESI-MS: 476/478 [M+H]$^+$ (LC-MS 1); $^1$H NMR (400 MHz, DMSO-d$_6$) δ ppm 1.95 (s, 3 H) 2.44 (s, 3H) 3.37 (s, 3 H) 3.85 (s, 3 H) 6.73 (s, 1 H) 6.88 (d, J=8.8 Hz, 1 H) 7.22 (d, J=8.1 Hz, 2 H) 7.32 (d, J=8.4 Hz, 2 H) 7.36 (d, J=1.6 Hz, 1 H) 7.6 (d, J=2.7 Hz, 1 H) 7.88 (dd, J=8.9, 2.8 Hz, 1 H) 8.32 (d, J=2.7 Hz, 1 H).

EXAMPLE 21a 6-(4-chlorophenyl)-5-(1,5-dimethyl-6-oxo-1,6-dihydropyridin-3-yl)-1-(2-methoxypyrimidin-5-yl)-3-methyl-5,6-dihydropyrrolo[3,4-c]pyrazol-4(1H)-one
and

EXAMPLE 21b 6-(4-chlorophenyl)-5-(1,5-dimethyl-6-oxo-1,6-dihydropyridin-3-yl)-2-(2-methoxypyrimidin-5-yl)-3-methyl-5,6-dihydropyrrolo[3,4-c]pyrazol-4(2H)-one

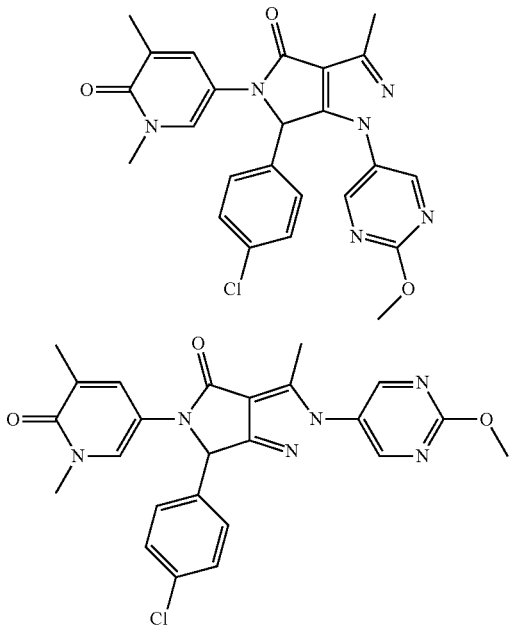

The title compounds 21a and 21b were prepared in analogy to the procedure described in Example 7 using 5-(5-chloro-1-methyl-6-oxo-1,6-dihydropyridin-3-yl)-6-(4-chlorophenyl)-3-methyl-5,6-dihydropyrrolo[3,4-c]pyrazol-4(2H)-one (Example 6) and (2-methoxypyrimidin-5-yl)-boronic acid. The mixture of regioisomers was separated by SFC (DEAP (250×30 mm, 5 μm), gradient 8-13% B in 11 min, A: scCO$_2$, B: MeOH; flow: 100 mL/min) to provide the title product 20a as a white solid. t$_R$: 1.008 min (UPLC 1); t$_R$: 0.87 min (LC-MS 1); ESI-MS: 477/479 [M+H]$^+$ (LC-MS 1); $^1$H NMR (400 MHz, DMSO-d$_6$) δ ppm $^1$H NMR (400 MHz, DMSO-d$_6$) δ ppm 1.95 (s, 3 H) 2.46 (s, 3 H) 3.37 (s, 3 H) 3.92 (s, 3 H) 6.74 (s, 1 H) 7.25 (d, J=8.4 Hz, 2 H) 7.32-7.38 (m, 3 H) 7.59-7.63 (m, 1 H) 7.62 (d, J=2.7 Hz, 1 H) 8.76 (s, 2 H) and 20b as a white solid. t$_R$: 0.976 min (UPLC 1); t$_R$: 0.86 min (LC-MS 1); ESI-MS: 477/479 [M+H]$^+$ (LC-MS 1); $^1$H NMR (400 MHz, DMSO-d$_6$) δ ppm 1.91 (s, 3 H) 2.46 (s, 3 H) 3.32 (s, 3 H) 3.96 (s, 3 H) 6.27 (s, 1 H) 7.29 (d, J=8.8 Hz, 2 H) 7.36 (d, J=8.8 Hz, 2 H) 7.42 (s, 1 H) 7.72 (s, 1 H) 8.63 (s, 2 H).

EXAMPLE 22

(R)-6-(4-chlorophenyl)-3-cyclopropyl-5-(1,5-dimethyl-6-oxo-1,6-dihydropyridin-3-yl)-1-(1-methyl-1H-pyrazol-5-yl)-5,6-dihydropyrrolo[3,4-c]pyrazol-4(1H)-one

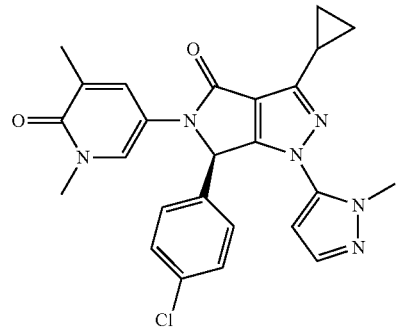 [SMILES: Cc1cc(N2C(=O)c3c(C4CC4)nn(-c4ccnn4C)c3[C@H]2c2ccc(Cl)cc2)cn(C)c1=O]

The title compound was obtained enantiomerically pure (>98% ee) after chiral preparative chromatography (system: Thar SFC200; column: Chiralpak AD-H 50×250 mm; mobile phase: scCO$_2$/IPA 75:25 (isocratic), flow: 200 g/min) of the racemic mixture of 6-(4-chlorophenyl)-3-cyclopropyl-5-(1,5-dimethyl-6-oxo-1,6-dihydropyridin-3-yl)-1-(1-methyl-1H-pyrazol-5-yl)-5,6-dihydropyrrolo[3,4-c]pyrazol-4(1H)-one (Example 5). (S)-6-(4-chlorophenyl)-3-cyclopropyl-5-(1,5-dimethyl-6-oxo-1,6-dihydropyridin-3-yl)-1-(1-methyl-1H-pyrazol-5-yl)-5,6-dihydropyrrolo[3,4-c]pyrazol-4(1H)-one, t$_R$: 1.55 min (system: Thar/Waters SFC Investigator MS; column: Chiralpak AD-H 4.6×250 mm; mobile phase: scCO$_2$/isopropanol 70:30 (isocratic), flow: 4 mL/min; detection UV: 215 nm). (R)-6-(4-chlorophenyl)-3-cyclopropyl-5-(1,5-dimethyl-6-oxo-1,6-dihydropyridin-3-yl)-1-(1-methyl-1H-pyrazol-5-yl)-5,6-dihydropyrrolo[3,4-c]pyrazol-4(1H)-one, t$_R$: 2.36 min (system: Thar/Waters SFC Investigator MS; column: Chiralpak AD-H 4.6×250 mm; mobile phase: scCO$_2$/isopropanol 70:30 (isocratic), flow: 4 mL/min; detection UV: 215 nm).

EXAMPLE 23

6-(4-chlorophenyl)-3-cyclopropyl-5-(1,5-dimethyl-6-oxo-1,6-dihydropyridin-3-yl)-5,6-dihydropyrrolo[3,4-c]pyrazol-4(1H)-one

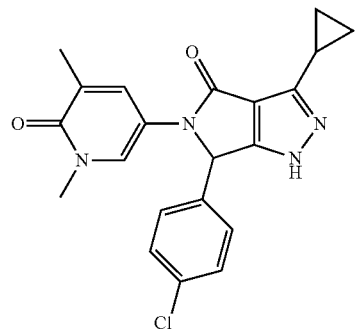 [SMILES: Cc1cc(N2C(=O)c3c(C4CC4)n[nH]c3C2c2ccc(Cl)cc2)cn(C)c1=O]

The title compound was prepared in analogy to the procedure described in Example 1 using 5-(4-chlorophenyl)-3-(cyclopropanecarbonyl)-1-(1,5-dimethyl-6-oxo-1,6-dihydropyridin-3-yl)pyrrolidine-2,4-dione (Step 1.3) and hydrazine. $t_R$: 0.81 min (LC-MS 1); ESI-MS: 395/397 [M+H]$^+$ (LC-MS 1); $^1$H NMR (400 MHz, DMSO-d$_6$) δ ppm 13.29 (s, 1H), 7.69 (d, J=2.8 Hz, 1 H), 7.44-7.33 (m, 3 H), 7.28-7.19 (m, 2 H), 6.13 (s, 1 H), 5.76, 3.36 (s, 3 H), 2.04 (m, 1 H), 1.93 (s, 3 H), 1.21-1.07 (m, 4 H).

EXAMPLE 24

(R)-6-(4-chlorophenyl)-3-cyclopropyl-5-(1,5-dimethyl-6-oxo-1,6-dihydropyridin-3-yl)-5,6-dihydropyrrolo[3,4-c]pyrazol-4(1H)-one

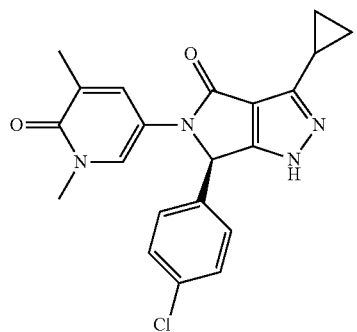 [SMILES: Cc1cc(N2C(=O)c3c(C4CC4)n[nH]c3[C@H]2c2ccc(Cl)cc2)cn(C)c1=O]

The title compound was obtained enantiomerically pure (>99% ee) after chiral preparative chromatography (system: Gilson PLC 2020; column: Chiracel OD-H 5 μm, 20×250 mm; mobile phase: heptane/EtOH/MeOH 80:10:10; flow: 10 mL/min; detection UV: 210 nm) of the racemic mixture of 6-(4-chlorophenyl)-3-cyclopropyl-5-(1,5-dimethyl-6-oxo-1,6-dihydropyridin-3-yl)-5,6-dihydropyrrolo[3,4-c]pyrazol-4(1H)-one (Example 23). (R)-6-(4-chlorophenyl)-3-cyclopropyl-5-(1,5-dimethyl-6-oxo-1,6-dihydropyridin-3-yl)-5,6-dihydropyrrolo[3,4-c]pyrazol-4(1H)-one. $t_R$: 7.13 min (system: Agilent HPLC; column: Chiracel OD-H 5 μm, 4.6×250 mm; mobile phase: heptane/EtOH/MeOH 80:10:10 (isocratic); flow: 1 mL/min; detection UV: 210 nm). (S)-6-(4-chlorophenyl)-3-cyclopropyl-5-(1,5-dimethyl-6-oxo-1,6-dihydropyridin-3-yl)-5,6-dihydropyrrolo[3,4-c]pyrazol-4(1H)-one. $t_R$: 9.95 min (system: Agilent HPLC; column: Chiracel OD-H 5 μm, 4.6×250 mm; mobile phase: heptane/EtOH/MeOH 80:10:10 (isocratic); flow: 1 mL/min; detection UV: 210 nm).

EXAMPLE 25

(R)-6-(4-chlorophenyl)-5-(1,5-dimethyl-6-oxo-1,6-dihydropyridin-3-yl)-1-(2-methoxypyridin-3-yl)-3-methyl-5,6-dihydropyrrolo[3,4-c]pyrazol-4(1H)-one

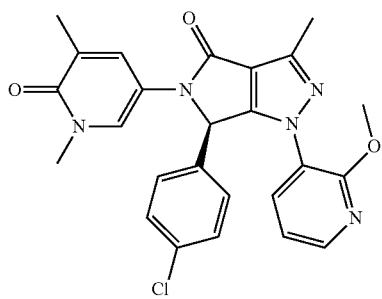 [SMILES: COc1ncccc1-n1nc(C)c2c1[C@@H](c1ccc(Cl)cc1)N(c1cc(C)c(=O)n(C)c1)C2=O]

The title compound was obtained enantiomerically pure (>99% ee) after chiral preparative chromatography (system: Mg II preparative SFC; column: Chiralpak AD-H 30×250 mm; mobile phase: scCO$_2$/MeOH 55:45 (isocratic), flow: 50 mL/min) of the racemic mixture 6-(4-chlorophenyl)-5-(1,5-dimethyl-6-oxo-1,6-dihydropyridin-3-yl)-1-(2-methoxypyridin-3-yl)-3-methyl-5,6-dihydropyrrolo[3,4-c]pyrazol-4(1H)-one (Example 17a). (S)-6-(4-chlorophenyl)-5-(1,5-dimethyl-6-oxo-1,6-dihydropyridin-3-yl)-1-(2-methoxypyridin-3-yl)-3-methyl-5,6-dihydropyrrolo[3,4-c]pyrazol-4(1H)-one, $t_R$: 2.34 min (system: Thar analytical SFC; column: Chiralpak AD-H 4.6×250 mm; mobile phase: scCO$_2$/MeOH (0.05% DEA) 50:50 (isocratic), flow: 2 mL/min; detection UV: 220 nm). (R)-6-(4-chlorophenyl)-5-(1,5-dimethyl-6-oxo-1,6-dihydropyridin-3-yl)-1-(2-methoxypyridin-3-yl)-3-methyl-5,6-dihydropyrrolo[3,4-c]pyrazol-4(1H)-one, $t_R$: 2.76 min (system: Thar analytical SFC; column: Chiralpak AD-H 4.6×250 mm; mobile phase: scCO$_2$/MeOH (0.05% DEA) 50:50 (isocratic), flow: 2 mL/min; detection UV: 220 nm).

EXAMPLE 26

(R)-6-(4-chlorophenyl)-5-(1,5-dimethyl-6-oxo-1,6-dihydropyridin-3-yl)-2-(2-methoxypyridin-3-yl)-3-methyl-5,6-dihydropyrrolo[3,4-c]pyrazol-4(2H)-one

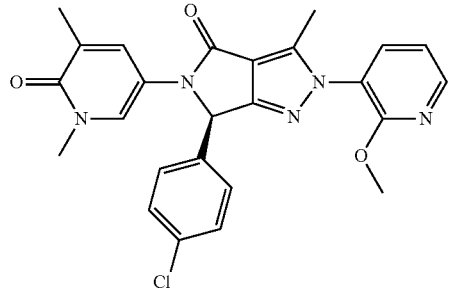 [SMILES: COc1ncccc1-n1nc2c(c1C)C(=O)N(c1cc(C)c(=O)n(C)c1)[C@@H]2c1ccc(Cl)cc1]

The title compound was obtained enantiomerically pure (>99% ee) after chiral preparative chromatography (system: Mg II preparative SFC; column: Chiralpak AD-H 30×250 mm; mobile phase: scCO$_2$/MeOH 55:45 (isocratic), flow: 50 mL/min) of the racemic mixture of 6-(4-chlorophenyl)-5-(1,5-dimethyl-6-oxo-1,6-dihydropyridin-3-yl)-2-(2-methoxypyridin-3-yl)-3-methyl-5,6-dihydropyrrolo[3,4-c]pyrazol-4(2H)-one (Example 17b). (S)-6-(4-chlorophenyl)-5-(1,5-dimethyl-6-oxo-1,6-dihydropyridin-3-yl)-2-(2-methoxypyridin-3-yl)-3-methyl-5,6-dihydropyrrolo[3,4-c]pyrazol-4(2H)-one, $t_R$: 4.75 min (system: Thar analytical SFC; column: Chiralpak AD-H 4.6×250 mm; mobile phase: scCO$_2$/MeOH (0.05% DEA) 50:50 (isocratic), flow: 2 mL/min; detection UV: 220 nm). (R)-6-(4-chlorophenyl)-5-(1,5-dimethyl-6-oxo-1,6-dihydropyridin-3-yl)-2-(2-methoxypyridin-3-yl)-3-methyl-5,6-dihydropyrrolo[3,4-c]pyrazol-4(2H)-one, $t_R$: 6.46 min (system: Thar analytical SFC; column: Chiralpak AD-H 4.6×250 mm; mobile phase: scCO$_2$/MeOH (0.05% DEA) 50:50 (isocratic), flow: 2 mL/min; detection UV: 220 nm).

EXAMPLE 27

(R)-6-(4-chlorophenyl)-5-(1,5-dimethyl-6-oxo-1,6-dihydropyridin-3-yl)-3-methyl-5,6-dihydropyrrolo[3,4-c]pyrazol-4(2H)-one

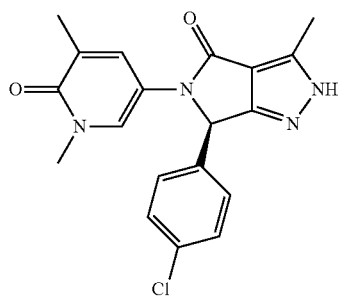 [SMILES: Cc1[nH]nc2c1C(=O)N(c1cc(C)c(=O)n(C)c1)[C@@H]2c1ccc(Cl)cc1]

The title compound was obtained enantiomerically pure (>99% ee) after chiral preparative chromatography (system: Gilson PLC 2020; column: Chiralpak IA 5 µm, 20×250 mm; mobile phase: heptane/EtOH 50:50; flow: 10 mL/min; detection UV: 220 nm) of the racemic mixture of 6-(4-chlorophenyl)-3-cyclopropyl-5-(1,5-dimethyl-6-oxo-1,6-dihydropyridin-3-yl)-5,6-dihydropyrrolo[3,4-c]pyrazol-4(1H)-one (Example 9). (S)-6-(4-chlorophenyl)-5-(1,5-dimethyl-6-oxo-1,6-dihydropyridin-3-yl)-3-methyl-5,6-dihydropyrrolo[3,4-c]pyrazol-4(2H)-one. $t_R$: 5.92 min (system: Agilent HPLC; column: Chiralpak IA 5 µm, 4.6×250 mm; mobile phase: heptane/EtOH 50:50 (isocratic); flow: 1 mL/min; detection UV: 220 nm). (R)-6-(4-chlorophenyl)-5-(1,5-dimethyl-6-oxo-1,6-dihydropyridin-3-yl)-3-methyl-5,6-dihydropyrrolo[3,4-c]pyrazol-4(2H)-one. $t_R$: 8.74 min (system: Agilent HPLC; column: Chiralpak IA 5 µm, 4.6×250 mm; mobile phase: heptane/EtOH 50:50 (isocratic); flow: 1 mL/min; detection UV: 220 nm).

EXAMPLE 28

(R)-5-(5-chloro-1-methyl-6-oxo-1,6-dihydropyridin-3-yl)-6-(4-chlorophenyl)-3-methyl-5,6-dihydropyrrolo[3,4-c]pyrazol-4(2H)-one

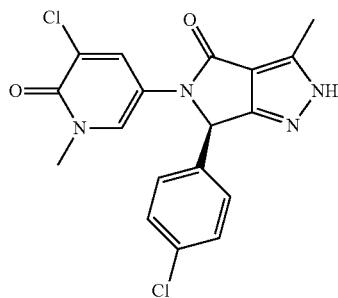 [SMILES: Cc1[nH]nc2c1C(=O)N(c1cc(Cl)c(=O)n(C)c1)[C@@H]2c1ccc(Cl)cc1]

The title compound was obtained enantiomerically pure (>99% ee) after chiral preparative chromatography (system: Gilson PLC 2020; column: Chiralpak ID 5 µm, 20×250 mm; mobile phase: heptane/EtOH 80:20; flow: 11 mL/min; detection UV: 210 nm) of the racemic mixture of 5-(5-chloro-1-methyl-6-oxo-1,6-dihydropyridin-3-yl)-6-(4-chlorophenyl)-3-methyl-5,6-dihydropyrrolo[3,4-c]pyrazol-4(2H)-one (Example 6). (S)-5-(5-chloro-1-methyl-6-oxo-1,6-dihydropyridin-3-yl)-6-(4-chlorophenyl)-3-methyl-5,6-dihydropyrrolo[3,4-c]pyrazol-4(2H)-one. $t_R$: 6.70 min (system: Merck HPLC; column: Chiralpak ID 5 µm, 4.6×250 mm; mobile phase: heptane/EtOH/MeOH 60:20:20 (isocratic); flow: 1 mL/min; detection UV: 210 nm). (R)-5-(5-chloro-1-methyl-6-oxo-1,6-dihydropyridin-3-yl)-6-(4-chlorophenyl)-3-methyl-5,6-dihydropyrrolo[3,4-c]pyrazol-4(2H)-one. $t_R$: 8.32 min (system: Merck HPLC; column: Chiralpak ID 5 µm, 4.6×250 mm; mobile phase: heptane/EtOH/MeOH 60:20:20 (isocratic); flow: 1 mL/min; detection UV: 210 nm).

Assays

The activity of a compound according to the present invention can be assessed by the following methods.

TR-FRET In-Vitro Binding Assays for BRD2, BRD3, and BRD4:

All assays were performed in 384 well microtiter plates. Each assay plate contained 8-point serial dilutions for 40 test compounds, plus 16 high- and 16 low controls. Liquid handling and incubation steps were done on an Innovadyne Nanodrop Express equipped with a robotic arm (Thermo CatX, Perkin Elmer/Caliper Twister II) and an incubator (Liconic STX40, Thermo Cytomat 2C450). The assay plates were prepared by addition of 50 nl per well of compound solution in 90% DMSO HummingBird nanodispenser (Zinsser Analytic). The assay was started by stepwise addition of 4.5 µl per well of bromo domain protein (50 mM HEPES, pH 7.5, 0.005% Tween20, 0.1% BSA, 50 mM NaCl, 45 nM His-Brd2(60-472) or 45 nM His-Brd3(20-477) or 45 nM His-Brd4(44-477) all proteins produced in-house) and 4.5 µl per well of peptide solution (50 mM HEPES, pH 7.5, 0.005% Tween20, 0.1% BSA, 50 mM NaCl, 60 nM acetyl-histone H4 (AcK 5, 8, 12, 16) (Biosyntan GmbH)). Reactions were incubated at 30° C. for 35 minutes. Subsequently 4.5 µl per well detection mix (50 mM HEPES, pH 7.5, 0.005% Tween20, 0.1% BSA, 50 mM NaCl, 3 nM Eu-labeled anti-His6 antibody, 21 nM streptavidin-allophycocyanin) were added. After 35 minutes incubation at 30° C., plates were measured in a Perkin Elmer EnVision multilabel reader. Concentrations causing 50% inhibition (1050) values were determined from percent inhibition values at different compound concentrations by non-linear regression analysis.

AlphaScreen In-Vitro Binding Assay for CREBBP

In order to assess bromodomain selectivity, we set up a binding assay using the bromodomain encoded by the CREBBP gene. Compounds were tested in the CREBBP assay with a similar protocol, however using AlphaScreen (Amplified Luminescent Proximity Homogeneous Assay, Perkin Elmer) as detection readout instead of TR-FRET. The assay was started by stepwise addition of 4.5 µl per well of bromo domain protein (50 mM HEPES, pH 7.5, 0.005% Tween20, 0.02% BSA, 150 mM NaCl, 324 nM His-CREBBP (1081-1197) (custom production at Viva Biotech Ltd.)) and 4.5 µl per well of peptide solution (50 mM HEPES, pH 7.5, 0.005% Tween20, 0.02% BSA, 150 mM NaCl, 120 nM acetyl-histone H4 (AcK 5, 8, 12) (Biosyntan GmbH)). Reactions were incubated at 30° C. for 35 minutes. Subsequently 4.5 µl per well detection mix (50 mM HEPES, pH 7.5, 0.005% Tween20, 0.02% BSA, 150 mM NaCl, 45 µg/ml Ni-chelate acceptor beads, 45 µg/ml streptavidin-donor beads) (Perkin Elmer)) were added. After 60 minutes incubation at room temperature, plates were measured in a Perkin Elmer EnVision multilabel reader. IC50 values were determined from percent inhibition values at different compound concentrations by non-linear regression analysis.

For further bromodomain selectivity profiling, additional panel assays were performed using analog protocols with minor modifications specific for the individual assay, using either TR-FRET or AlphaScreen for detection.

Preparation of Compound Dilutions

Test compounds were dissolved in DMSO (10 mM) and transferred into 1.4 mL flat bottom or V-shaped Matrix tubes carrying a unique 2D matrix. The stock solutions were stored at +2° C. if not used immediately. For the test procedure the vials were defrosted and identified by a scanner whereby a working sheet was generated that guided the subsequent working steps. Compound dilutions were made in 96 well plates. This format enabled the assay of maximally 40 individual test compounds at 8 concentrations (single points) including 4 reference compounds, if desired (known BET inhibitors from the prior art, for this and other assays of the type disclosed herein). The dilution protocol included the production of "pre-dilution plates", "master plates" and "assay plates".

Pre-dilution plates: 96 polypropylene well plates were used as pre-dilution plates. A total of 4 pre-dilution plates were prepared including 10 test compounds each on the plate positions A1-A10, one standard compound at A11 and one DMSO control at A12. All dilution steps were done on a HamiltonSTAR robot.

Master plates: 30 µL of individual compound dilutions including standard compound and controls of the 4 "pre-dilution plates" were transferred into a 384 "master plate" including the following concentrations 10000, 3003, 1000, 300, 100, 30, 10 and 3 µM, respectively in 90% of DMSO. Assay plates: Identical "assay plates" were then prepared by pipetting 50 nL each of compound dilutions of the "master plates" into 384-well "assay plates" by means of a HummingBird 384-channel dispenser. These plates were used directly for the assay which was performed in a total volume of 13.55 µL. This led to a final compound concentration of 37, 11, 3.7, 1.1, 0.37, 0.11, 0.037 and 0.011 µM and a final DMSO concentration of 0.37% in the assay.

Cell Growth Inhibition Assay

The human leukemia cell lines MV-4-11, THP-1 and K-562 were employed to characterize the effect of BET inhibitors on cellular proliferation and viability. Cells were obtained from the American Type Culture Collection (ATCC) and cultured at 37° C. in a humidified 5% $CO_2$ incubator in the following media: MV-4-11: DMEM high glucose (Animed #1-26F01-I), 10% FCS (Animed #2-01F26-I), 4 mM L-Glutamine (Animed #5-10K50), 1 mM Sodium Pyruvate (Animed # G03625P), 1× Penicillin-Streptomycin (Animed # F12478P); K-562: Iscove's MEM (Animed #1-28F16-I), 10% FCS (Animed #2-01F26-I), 4 mM L-Glutamine (Animed #5-10K50), 1× Penicillin-Streptomycin (Animed # F12478P); THP-1: RPMI-1640 (Animed #1-41F01-I), 10% FCS (Animed #2-01F26-I), 2 mM L-Glutamine (Animed #5-10K50), 10 mM HEPES (Animed #5-31F100), 1 mM Sodium Pyruvate (Animed # G03625P), 1× Penicillin-Streptomycin (Animed # F12478P). The AML lines MV-4-11 and THP-1 are very sensitive to BET inhibitors and show massive cell death upon BET inhibition (Zuber et al., Nature, 478 (2011), 524-8). Compound-mediated suppression of cell proliferation/viability was assessed by quantification of cellular ATP levels using the CellTiter-Glo (CTG) reagent (Promega). Briefly, cells were seeded in 20 µl fresh medium into 384-well plates, followed by addition of 5 µl medium containing compound dilutions at 5-fold their final intended concentration. Dose-response effects were assessed by 3-fold serial dilutions of the test compound, starting at 10 µM. Following incubation of the cells for 4 days at 37° C. and 5% $CO_2$, the effect of inhibitors on cell viability was quantified following addition of 20 µl CTG and luminescence quantification (integration time: 100 ms) as per vendor manual, using a correspondingly equipped Tecan M200 multi-mode platereader (TECAN, Switzerland). For data analysis, the assay background value determined in wells containing medium, but no cells, was subtracted from all data points. To enable differentiation of cytotoxic from cytostatic compounds, the number of viable cells is assessed relative to that observed at the time of compound addition using a separate cell plate (day 0). The effect of a particular test compound concentration on cell proliferation/viability is expressed as percentage of the background- and day 0-corrected luminescence reading obtained for cells treated with vehicle only (DMSO, 0.1% final concentration), which is set as 100%, whereas that luminescence reading for wells containing medium is set as −100%. Compound concentrations leading to half-maximal (1050) and total growth inhibition (TGI) were determined using standard four parameter curve fitting.

Nut-Foci Formation Assay

HCC2494 NUT midline carcinoma cells (expressing BRD4-NUT-fusion) were obtained from the University of Texas Southwestern and cultured in RPMI-1640 medium containing 10% Foetal Calf Serum at 37° C. in a humidified 5% $CO_2$ incubator.

Compound-mediated inhibition of BRD4 activity was monitored by quantification of the number and intensity of nuclear BRD4-NUT foci using automated immunofluorescence microscopy. Briefly, 5000 cells in 20 µl fresh medium were seeded into Poly-D-Lysine-precoated 384-well plates and incubated overnight at 37° C. and 5% $CO_2$, followed by addition of 5 µl medium containing compound dilutions at 5-fold their final intended concentration. Dose-response effects were assessed by 3-fold serial dilutions of the test compound, starting at 10 µM. Following incubation of the cells for 24 hours at 37° C. and 5% $CO_2$, the cells were fixed by incubation with 3.7% formaldehyde for 10 min, followed by immunofluorescence staining using rabbit anti-NUT (Cell Signaling Technologies, Cat#3625) as primary, and AlexaFluor488-labeled goat anti-rabbit (Invitrogen, Cat#A11008) as secondary antibody (latter complemented with 1 µg/mL Hoechst33342 as DNA dye). Assay plates were imaged using the appropriate filter sets on the Cellomics VTi automated fluorescence microscopy platform (ThermoFisher Scientific) and the population average of the number of NUT-foci per nucleus is quantified using the Cellomics Spot Detection BioApplication image analysis algorithm (ThermoFisher Scientific). The effect of a particular test compound concentration on NUT-foci number and intensity is expressed as percentage of the value obtained for cells treated with vehicle only (DMSO, 0.1% final concentration), which was set as 100. Compound concentrations leading to half-maximal (1050) inhibition of the aforementioned readout parameters were determined using standard four parameter curve fitting.

Using the biochemical and cellular assays as described in this application compounds of the invention exhibit inhibitory efficacy in accordance to Tables 1 and 2, provided infra.

TABLE 1

Biochemical IC50 values*

| Example | BRD4 | BRD2 | BRD3 | CREBBP |
|---|---|---|---|---|
| 1 | 0.028 | 0.032 | 0.03 | 1.4 |
| 2 | 0.016 | 0.022 | 0.02 | 1.2 |
| 3 | 0.043 | 0.042 | 0.034 | |
| 4 | 0.014 | 0.015 | 0.013 | 3 |
| 5 | 0.096 | 0.074 | 0.082 | 5 |
| 6 | 0.12 | 0.094 | 0.08 | 4.1 |
| 7a | 0.11 | 0.076 | 0.065 | 4.4 |
| 7b | 0.041 | 0.032 | 0.024 | 1.9 |
| 8a | 0.17 | 0.12 | 0.12 | >37 |
| 8b | 0.21 | 0.16 | 0.14 | 5.4 |
| 9 | 0.09 | 0.072 | 0.067 | 3 |
| 10 | 0.089 | 0.084 | 0.062 | 3 |
| 11 | 0.04 | 0.038 | 0.034 | 1.9 |
| 12 | 0.067 | 0.052 | 0.046 | 1.4 |
| 13 | 0.103 | 0.097 | 0.0755 | 2.2 |
| 14 | 0.1 | 0.094 | 0.074 | 5.1 |
| 15 | 0.0625 | 0.07 | 0.0655 | 1 |
| 16 | 0.056 | 0.0485 | 0.052 | 0.545 |
| 17a | 0.086 | 0.078 | 0.064 | 4 |
| 17b | 0.056 | 0.053 | 0.046 | 1.3 |
| 18a | 0.079 | 0.068 | 0.062 | 3.1 |
| 18b | 0.041 | 0.035 | 0.039 | 1.3 |
| 19 | 0.1 | 0.08 | 0.073 | 3.8 |
| 20a | 0.062 | 0.061 | 0.05 | 2 |
| 20b | 0.056 | 0.049 | 0.048 | 3 |
| 21a | 0.071 | 0.063 | 0.052 | >11.1 |
| 21b | 0.11 | 0.1 | 0.094 | 4.7 |
| 22 | 0.14 | 0.16 | 0.089 | 2.9 |
| 23 | | 0.052 | 0.049 | 3.3 |
| 24 | 0.073 | 0.074 | 0.047 | 1.7 |
| 25 | 0.15 | 0.13 | 0.064 | 2 |
| 26 | 0.091 | 0.11 | 0.052 | 1 |
| 27 | 0.037 | 0.037 | 0.027 | 1.2 |
| 28 | 0.16 | 0.17 | 0.069 | 2.2 |

*Values from either single determination or n ≥ 2 independent determinations

TABLE 2

Cellular IC50 values*

| Example | MV-4-11 GI50 (μM) | MV-4-11 TGI (μM) | THP-1 GI50 (μM) | THP-1 TGI (μM) | K-562 GI50 (μM) | K-562 TGI (μM) | HCS Brd4-NUT IC50 (μM) |
|---|---|---|---|---|---|---|---|
| 1 | 0.0246 | 0.0412 | 0.0449 | 0.104 | 0.141 | >10 | 0.0333 |
| 2 | 0.0154 | 0.0303 | 0.0219 | 0.0468 | 0.121 | >10 | 0.0201 |
| 3 | 0.0375 | 0.064 | 0.0901 | 0.264 | 0.268 | >10 | 0.049 |
| 4 | 0.0205 | 0.0336 | 0.0456 | 0.1 | 0.109 | >10 | 0.0299 |
| 5 | 0.0538 | 0.1 | 0.101 | 0.179 | 0.658 | >10 | 0.138 |
| 6 | 0.0741 | 0.134 | 0.189 | 0.352 | 0.558 | >10 | 0.108 |
| 7a | 0.0877 | 0.121 | 0.204 | 0.384 | 0.719 | >10 | 0.0609 |
| 7b | 0.0567 | 0.0824 | 0.104 | 0.285 | 0.548 | >10 | 0.0744 |
| 8a | 0.141 | 0.294 | 0.127 | 0.493 | 0.991 | >10 | 0.298 |
| 8b | 0.117 | 0.195 | 0.293 | 0.562 | 0.999 | >10 | 0.058 |
| 9 | 0.051 | 0.0721 | 0.0885 | 0.206 | 0.322 | >10 | 0.0438 |
| 10 | 0.0394 | 0.0655 | 0.0764 | 0.132 | 0.336 | >10 | 0.108 |
| 11 | 0.0186 | 0.0294 | 0.0366 | 0.0822 | 0.127 | >10 | 0.0417 |
| 12 | 0.0191 | 0.0374 | 0.0622 | 0.112 | 0.193 | >10 | 0.0484 |
| 13 | 0.03 | 0.0562 | 0.0698 | 0.119 | 0.484 | >10 | |
| 14 | 0.122 | 0.203 | 0.219 | 0.352 | 0.615 | >10 | |
| 15 | 0.0546 | 0.0924 | 0.0678 | 0.143 | 0.64 | >10 | 0.0607 |
| 16 | 0.0236 | 0.0437 | 0.043 | 0.0922 | 0.197 | >10 | 0.0606 |
| 17a | 0.0581 | 0.0879 | 0.102 | 0.175 | 0.293 | >10 | 0.0561 |
| 17b | 0.027 | 0.0343 | 0.0724 | 0.117 | 0.154 | >10 | 0.0403 |
| 18a | 0.0893 | 0.101 | 0.0896 | 0.175 | 0.574 | >10 | 0.0666 |
| 18b | 0.0169 | 0.0313 | 0.044 | 0.0931 | 0.149 | >10 | 0.0217 |
| 19 | 0.0505 | 0.0798 | 0.091 | 0.164 | 0.302 | >10 | 0.0667 |
| 20a | 0.0496 | 0.065 | 0.104 | 0.178 | 0.236 | >10 | 0.0736 |
| 20b | 0.0386 | 0.0542 | 0.0931 | 0.156 | 0.239 | >10 | 0.0576 |
| 21a | 0.115 | 0.177 | 0.166 | 0.331 | 0.404 | >10 | |
| 21b | 0.105 | 0.208 | 0.209 | 0.396 | 0.51 | >10 | |
| 22 | 0.0495 | 0.08865 | 0.0874 | 0.165 | 0.2775 | >10 | |
| 23 | 0.0256 | 0.048 | 0.05935 | 0.1285 | 0.1695 | >10 | |
| 24 | 0.02155 | 0.03495 | 0.0297 | 0.06225 | 0.10305 | >10 | |
| 25 | 0.0407 | 0.07255 | 0.0727 | 0.1355 | 0.206 | >10 | |
| 26 | 0.02255 | 0.03675 | 0.0276 | 0.0524 | 0.1735 | >10 | |
| 27 | 0.0271 | 0.0496 | 0.0562 | 0.115 | 0.112 | >10 | |
| 28 | 0.0493 | 0.0864 | 0.10965 | 0.2015 | 0.318 | >10 | |

*Values from either single determination or n ≥ 2 independent determinations

What is claimed is:

1. A compound of formula (I) or a pharmaceutically acceptable salt thereof,

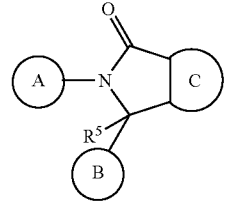

wherein
A is

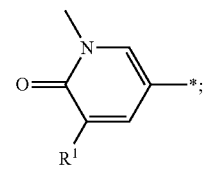

B is

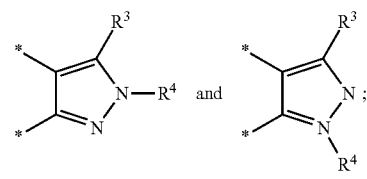

C is selected from:

R¹ is selected from methyl and chloro;
R² is selected from chloro and fluoro;
R³ is selected from methyl and cyclopropyl; and R⁴ is selected from H; (C₁-C₄)alkyl optionally substituted by —OH or —O—(C₁-C₄)alkyl; cyclopropyl;
and

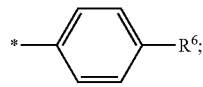

R⁵ is H;
R⁶ is —O—(C₁-C₄)alkyl;
R⁷ is selected from H and methoxy;
and * indicates the point of attachment to the remainder of the molecule.

2. A compound of formula (I), or a pharmaceutically acceptable salt thereof, according to claim 1, wherein R² is chloro.

3. A compound of formula (I), or a pharmaceutically acceptable salt thereof, according to claim 1, wherein R³ is selected from methyl and cyclopropyl.

4. A compound of formula (I), or a pharmaceutically acceptable salt thereof, according to claim 1, wherein R⁴ is selected from methyl, ethyl, isopropyl, —CH₂CH₂OH, —CH₂CH₂OCH₃, cyclopropyl,
and

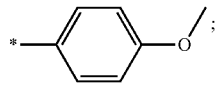

or R⁴ is H.

5. A compound of formula (I), or a pharmaceutically acceptable salt thereof, according to claim 1, selected from:
Example 1: 6-(4-chlorophenyl)-3-cyclopropyl-5-(1,5-dimethyl-6-oxo-1,6-dihydropyridin-3-yl)-1-methyl-5,6-dihydropyrrolo[3,4-c]pyrazol-4(1H)-one;
Example 2: (R)-6-(4-chlorophenyl)-3-cyclopropyl-5-(3,8-dimethyl-[1,2,4]triazolo[4,3-a]pyridin-6-yl)-1-methyl-5,6-dihydropyrrolo[3,4-c]pyrazol-4(1H)-one;
Example 3: 6-(4-chlorophenyl)-3-cyclopropyl-5-(1,5-dimethyl-6-oxo-1,6-dihydropyridin-3-yl)-1-(2-hydroxyethyl)-5,6-dihydropyrrolo[3,4-c]pyrazol-4(1H)-one;
Example 4: 6-(4-chlorophenyl)-3-cyclopropyl-5-(1,5-dimethyl-6-oxo-1,6-dihydropyridin-3-yl)-1-(2-methoxyethyl)-5,6-dihydropyrrolo[3,4-c]pyrazol-4(1H)-one;
Example 6: 5-(5-chloro-1-methyl-6-oxo-1,6-dihydropyridin-3-yl)-6-(4-chlorophenyl)-3-methyl-5,6-dihydropyrrolo[3,4-c]pyrazol-4(2H)-one;
Example 9: 6-(4-chlorophenyl)-5-(1,5-dimethyl-6-oxo-1,6-dihydropyridin-3-yl)-3-methyl-5,6-dihydropyrrolo[3,4-c]pyrazol-4(2H)-one;
Example 10: 6-(4-chlorophenyl)-5-(1,5-dimethyl-6-oxo-1,6-dihydropyridin-3-yl)-1,3-dimethyl-5,6-dihydropyrrolo[3,4-c]pyrazol-4(1H)-one;
Example 11: 6-(4-chlorophenyl)-1-cyclopropyl-5-(1,5-dimethyl-6-oxo-1,6-dihydropyridin-3-yl)-3-methyl-5,6-dihydropyrrolo[3,4-c]pyrazol-4(1H)-one;
Example 12: 6-(4-chlorophenyl)-5-(1,5-dimethyl-6-oxo-1,6-dihydropyridin-3-yl)-1-isopropyl-3-methyl-5,6-dihydropyrrolo[3,4-c]pyrazol-4(1H)-one;
Example 13: 6-(4-chlorophenyl)-5-(1,5-dimethyl-6-oxo-1,6-dihydropyridin-3-yl)-1-(4-methoxy-phenyl)-3-methyl-5,6-dihydropyrrolo[3,4-c]pyrazol-4(1H)-one;
Example 23: 6-(4-chlorophenyl)-3-cyclopropyl-5-(1,5-dimethyl-6-oxo-1,6-dihydropyridin-3-yl)-5,6-dihydropyrrolo[3,4-c]pyrazol-4(1H)-one;
Example 24: (R)-6-(4-chlorophenyl)-3-cyclopropyl-5-(1,5-dimethyl-6-oxo-1,6-dihydropyridin-3-yl)-5,6-dihydropyrrolo[3,4-c]pyrazol-4(1H)-one;
Example 27: (R)-6-(4-chlorophenyl)-5-(1,5-dimethyl-6-oxo-1,6-dihydropyridin-3-yl)-3-methyl-5,6-dihydropyrrolo[3,4-c]pyrazol-4(2H)-one; and
Example 28: (R)-5-(5-chloro-1-methyl-6-oxo-1,6-dihydropyridin-3-yl)-6-(4-chlorophenyl)-3-methyl-5,6-dihydropyrrolo[3,4-c]pyrazol-4(2H)-one.

6. A pharmaceutical composition comprising a therapeutically effective amount of a compound according to claim 1 or a pharmaceutically acceptable salt thereof and one or more pharmaceutically acceptable carriers.

* * * * *